US008268792B2

(12) United States Patent
Heger et al.

(10) Patent No.: US 8,268,792 B2
(45) Date of Patent: Sep. 18, 2012

(54) USE OF AN ACTIVE INGREDIENT COMBINATION THAT CONTAINS HYDROXYSTILBENE FOR PREVENTING AND/OR TREATING DISEASES

(75) Inventors: Peter Heger, Ubstadt-Weiher (DE); Reinhard Rettenberger, Göppingen (DE); Carl-Friedrich Spaich, Heiningen (DE)

(73) Assignees: Peter Heger, Ubstadt-Weiher (DE); Carl-Friedrich Spaich, Heiningen (DE); Reinhard Rettenberger, Goppingen (DE)

( * ) Notice: Subject to any disclaimer, the term of this patent is extended or adjusted under 35 U.S.C. 154(b) by 845 days.

(21) Appl. No.: 11/883,685

(22) PCT Filed: Feb. 3, 2006

(86) PCT No.: PCT/EP2006/000951
§ 371 (c)(1),
(2), (4) Date: May 15, 2008

(87) PCT Pub. No.: WO2006/082068
PCT Pub. Date: Aug. 10, 2006

(65) Prior Publication Data
US 2009/0042817 A1    Feb. 12, 2009

(30) Foreign Application Priority Data

Feb. 4, 2005   (DE) .......................... 10 2005 005 268
Feb. 4, 2005   (DE) .......................... 10 2005 005 270
Feb. 4, 2005   (DE) .......................... 10 2005 005 271
Feb. 4, 2005   (DE) .......................... 10 2005 005 273
Feb. 4, 2005   (DE) .......................... 10 2005 005 274
Feb. 4, 2005   (DE) .......................... 10 2005 005 275
Feb. 4, 2005   (DE) .......................... 10 2005 005 276
May 19, 2005   (DE) .......................... 10 2005 023 164

(51) Int. Cl.
*A61K 31/05*   (2006.01)
*A61P 25/24*   (2006.01)

(52) U.S. Cl. .......................................... 514/35; 514/733
(58) Field of Classification Search ................. 514/35, 514/733
See application file for complete search history.

(56) References Cited

U.S. PATENT DOCUMENTS

| 2008/0248069 A1 | 10/2008 | Heger et al. |
| 2009/0048184 A1 | 2/2009 | Heger et al. |
| 2009/0137496 A1 | 5/2009 | Heger et al. |

FOREIGN PATENT DOCUMENTS

| AU | 2628177 | 1/1979 |
| EP | 1 140 097 | 10/2001 |
| EP | 1 161 944 | 12/2001 |
| FR | 2 835 185 A | 8/2003 |
| FR | 2835185 | * 8/2003 |
| WO | WO-97/44407 | 11/1997 |
| WO | WO 03/039557 A | 5/2003 |
| WO | WO 03/039557 A1 | * 5/2003 |
| WO | WO 2006/082071 A1 | 8/2006 |

OTHER PUBLICATIONS

Konig, J.E. et al, The Prostate, 2004, 58, 121-129.*
Aggarwal et al, Anticancer Research, 2004, 24, 2783-2840.*
Reuter et al Ann. Neurol. 2002, 51, 507-516.*
Enmark, E. et al., "Human Estrogen Receptor β-Gene Structure, Chrmosomal Localization, and Expression Pattern," J. Clin. Endocrinol. Metab. 1997; 82: 4258-4265.
Frasor, J. et al., "Response-Specific and Ligand Dose-Dependent Modulation of Estrogen Receptor (ER) α Activity by ERβ in the Uterus," Endocrinol. 2003; 144: 3159-3166.
Galien, R. et al., "Estrogen receptor impairs interleukin-6 expression by preventing protein binding on the NF-κB site," Nucleic Acids Res. 1997; 25: 2434-2439.
Gao, S. et al., "Modulation of Androgen Receptor-Dependent Transcription by Resveratrol and Genistein in Prostate Cancer Cells," The Prostate 2004; 59: 214-225.
George, D.J. et al., "The Prognostic Significance of Plasma Interleukin-6 Levels in Patients with Metastatic Hormone-Refractory Prostate Cancer: Results from Cancer and Leukemia Group B 9480," Clin Cancer Res 2005, 11: 1815-1820.
Gilbert, C., "Major human cancers are preventable: physiological stimuli induce a dopamine-thyroid-immune efficient mechanism," E J. Cancer Prev 1997; 6: 269-276 (abstract).
Guerini, V. et al., "The Androgen Derivative 5α-Androstane-3β, 17β-Diol Inhibits Prostate Cancer Cell Migration Through Activation of the Estrogen Receptor β Subtype," Cancer Res 2005; 65: 5445-5453.
Hanstein, B. et al., "Insights into the molecular biology of the estrogen receptor define novel therapeutic targets for breast cancer," Eur. J. Endocrinol. 2004; 150: 243-255.
Harris, H.A. et al., "A selective estrogen receptor-β agonist causes lesion regression in an experimentally induced model of endometriosis," Hum. Reprod. 2005; 20: 936-941.
Harris, H.A. et al., "Evaluation of an Estrogen Receptor-β Agonist in Animal Models of Human Disease," Endocrinol. 2003; 144: 4241-4249.
Henderson, T.A. et al., "Steroid Receptor Expression in Uterine Natural Killer Cells," J. Clin. Endocrinol. Metab. 2003; 88: 440-449.
Imamov, O. et al., "Estrogen Receptor β in Prostate Cancer," N. Engl. J. Med. 2004; 351: 2773-2774.
Imwalle, D.B. et al., "Lack of functional estrogen receptor β influences anxiety behavior and serotonin content in female mice," Physiology & Behavior 2005; 84: 157-163.
Jiang, X. P. et al., "Recuction in Serum IL-6 After Vacination of Breast Cancer aPatients with Tumour-Associated Antigens is Related to Estrogen Receptor Status," Cytokine 2000; 12: 458-465.

(Continued)

*Primary Examiner* — Shaojia Anna Jiang
*Assistant Examiner* — Ganapathy Krishnan
(74) *Attorney, Agent, or Firm* — Edwards Wildman Palmer LLP; Peter C. Lauro, Esq.; Weiying Yang, Esq.

(57) ABSTRACT

The invention relates to the use of a combination of active ingredients, consisting essentially of rhaponticin and deoxyrhaponticin, their functional derivatives or the stereoisomeric forms thereof, in the form of salts or phenol respectively, for producing an agent for the prevention and/or treatment of diseases, whose occurrence and/or progress is associated with an increased IL-6 serum level and/or whose occurrence and/or progress can be treated by a dose of a selective oestrogen receptor β (ER-β) agonist.

10 Claims, 8 Drawing Sheets

OTHER PUBLICATIONS

Konig, J.E. et al., "Analysis of the Inflammatory Network in Benign Prostate Hyperplasia and Prostate Cancer," Prostate, 2004; 58: 121-129.
Krege, J. H. et al., "Generation and reproductive phenotypes of mice lacking estrogen receptor β," Proc. Natl. Acad. Sci USA, 1998; 95: 15677-15682.
Kuiper, G. G. J. M. et al., "Comparison of the Ligand Binding Specificity and Transcript Tissue Distribution of Estrogen Receptors α and β," Endocrinol. 1997, 138: 863-870.
Kuiper, G. G. J. M. et al., "Cloning of a novel estrogen receptor expressed in rat prostate and ovary," Proc. Natl. Acad. Sci, USA, 1996; 93: 5925-5930.
Lepor, H., "Phase III Multicenter Placebo-Controlled Study of Tamsulosin in Benign Prostatic Hyperplasia," Urology 1998; 51 (6): 892-900.
Long, R and Gardam, M., "Tumour necrosis factor-α inhibitors and the reactivation of latent tuberculosis infection," CMAJ 2003; 168: 1153-1156.
Lund, T.D. et al., "Novel Actions of Estrogen Receptor-β on Anxiety-Related Behaviors," Endocrinology 2005; 146: 797-807.
Matsuda, H. et al., "Study on Anti-Oketsu Activity on Rhubarb II. Anti-allergic Effects of Stilbene Components from Rhei undulati Rhizoma (Dried Rhizome of Rheum undulatum Cultivated in Korea)," Biol. Pharm. Bull. 2001, 24(3)): 264-267.
Million women Study Collaborators: "Breast cander and hormone-replacement therapy in the Million Women Study," Lancet 2003; 362: 419-427.
Morris, G. Z. et al., "Resveratrol Induces Apoptosis in LNCaP Cells and Requires Hydroxyl Groups to Decrease Viability in LNCaP and DU 145 Cells," The prostate 2002, 52, 319-329.
Motivala, S. J. et al., "Inflammatory Markers and Sleep Disturbance in Major Depression," Psychosom Med 2005; 67: 187-194.
Park, Woo-Chan and Jordan, V. Craig, "Selective estrogen receptor modulators (SERMS) and their roles in breast cancer prevention," Trends Mol. Medicine 2002; 8: 82-88.
Park, Eun-Kyung et al., "Antithrombotic and Antiallergic Activities of Phaponticin from Rhei Rhizoma Are Activated by Human Intestinal Bacteria," Arch. Pharm. Res. 2002, 25(4), 528-533.
Peters, D. J. and Sorkin, E. M., "Finasteride," Drugs 1993; 46: 177-208.
Pfeilschifter, J. et al., "Changes in Proinflammatory Cytokine Activity after Menopause," Endocrine Rev. 2002; 23: 90-119.
Reuter, U. et al., "Nuclear Factor-κB as a Molecular Target for Migraine Therapy," Ann Neurol 2002; 51: 507-516.
Roberti, M. et al., "Synthesis and Biological Evaluation of Resveratrol and Analogues as Apoptosis-Inducing Agents," J. Med. Chem. 2003, 46, 3546-3554.
Rocha, B.A. et al., "17beta-Estradiol-induced antidepressant-like effect in the Forced Swim Test is absent in estrogen receptor-beta knockout (BERKO) mice," Psychopharmacology 2005, 179: 637-643 (abstract).
Siddiqui, E.J. et al., "The role of serotonin in tumour growth (review)," Oncol Rep 2005; 14: 1593-1597 (abstract).
Spinelli, M.G., "Depression and Hormone Therapy," Clin Obstet Gynecol 2004; 47: 428-436.
Stein, B. and Yang, M.X., "Repression of the Interleukin-6 Promoter by Estrogen Receptor is Mediated by NF-κB and C/EBPβ," Mol Cell Biol. 1995; 15: 4971-4979.
Stygar, D. et al., "Co-localization of oestrogen receptor β and leukocyte markers in the human cervix," Mol. Hum. Reprod. 2001; 7: 881-886.
Trikha, M. et al., "Targeted Anti-Interleukin-6 momoclonal Antibody Therapy for Cancer: A Review of the Rationale and Clinical Evidence," Clin Cancer Res. 2003; 9: 4653-4665.
Unfer, V. et al., "Endometrial effects of long-term treatment with phytoestrogens: a randomized, double-blind, placebo-controlled study," Fertil Seril 2004; 82: 145-148.
Vegeto, E. et al., "Estrogen Prevents the Lipopolysaccharide-Induced Inflammatory Response in Microglia," J. Neurosci. 2001; 21: 1809-1818.
Walf, A.A. and Frye, C.A., "Erβ-Selective Estrogen Receptor Modulators Produce Antianxiety Behavior when Administered Systemically to Ovariectomized Rats," Neuropsychopharmacology 2005; 30: 1598-1609.
Weihua, Z. et al., An endocrine pathway in the prostate, ERβ, AR, 5α-androstane-3β, 17ζ-diol, and CYP7B!, regulates prostate growth,: Proc. Natl. Acad. Sci USA, 2002; 99: 13589-13594.
Wen, Y. et al., "Estrogen attenuates nuclear factor-kappa B activation induced by transient cerebral ischemia," Brain Res. 2004; 1008: 147-154.
Writing Group for the Women's Health Initiative Investigators, "Risks and Benefits of Estrogen Plus Progestin in Healthy Postmenopausal Women," JAMA 2002; 288: 321-333.
Miller & O'Callaghan, Metab Clin Exp 2005; 54: 33-38.
Anonym: "Phytoestrogen hilft bei Beschwerden im Klimakterium" Arzte Zeitung, [Online] May 16, 2000, XP002378130, Retrieved from the Internet.
Kageura T et al: "Inhibitors from rhubarb on lipopolysaccaride-induced nitric oxide production in macrophages: Structural requiements of stilbenes for the activity" Bioorganic and Medicinal Chemistry 2001 United Kingdom, vol. 9 No. 7, 2001, pp. 1887-1893, XP002378711, ISSN: 0968-0896.
Ko S K et al: "Effects of stilbene derivatives from Rheum undulatum on carrageenan-induced acute edema in rats" Korean Journal of Pharmacognosy 2004 South Korea, vol. 35, No. 2, 2004, pp. 171-174, XP009065748, ISSN: 0253-3073.
Ryu S Y et al: "Antititumor activity of some phenolic components in plants" Archives of Pharmacal Research Natl. Fisheries University, Pusan, KR. vol. 17, No. 1, Jan. 1994, pp. 42-44, XP002968965, ISSN: 0253-6269.
Chun Young Jin et al: "Mechanism-based inhibition of human cytochrome P450 1A1 by rhapontigenin" Drug Metabolism and Disposition, vol. 29, No. 4 Part 1, Apr. 2001, pp. 389-393, XP002378712, ISSN: 0090-9556.
Waffo-Teguo Pierre et al: "Potential cancer-chemopreventive activities of wine stilbenoids and flavans extracted from grape (Vitis vinifera) cell cultures" Nutrition and Cancer, vol. 40, No. 2, 2001, pp. 173-179, XP009065742, ISSN: 0163-5581.
Aggarwal B B et al: "Role of resveratrol in prevention and therapy of cancer: Preclinical and clinical studies", Anticancer Research 2004 Greece, vol. 24, No. 5 A, 2004, pp. 2783-2840, XP009065753, ISSN: 0250-7005.
Masuda et al., "Phytoestrogens from the Roots of Polygonum cuspidatum (Polygonaceae): Structure-Requirement of Hydroxyanthraquinones for Estrogenic Activity", Bioorganic & Medicinal Chemistry Letters, 11 (2001) 1839-1842.
Masuda et al., "Microsomal transformation of emodin into a direct mutagen." (Abstract), Mutat Res. Feb. 1984; 125(2): 135-44.
Donnelly, et al., "Anti-inflammatory effects of resveratrol in lung epithelial cells: molecular mechanisms", Am J Physiol Lung Cell Mol Physiol 287 (2004): L774-L783.
Park et al., "Antithrombotic and Antiallergic Activities of Rhaponticin from Rhei Rhizoma are Activated by Human Intestinal Bacteria", Arch Pharm Res vol. 25, No. 4, (2002): 528-533.
Sugiyama, et al., "ERβ: recent understanding of estrogen signaling", Trends in Endo. and Metabolism, 21 (2010): 545-552.
Obi, et al., "The Use of Herbal Preparations to Alleviate Climacteric Disorders and Risk of Postmenopausal Breast Cancer in a German Case-Control Study", Cancer Epidemiol Biomarkers Prev. 2009, 18(8), 2207-2213.
Alesci, S. et al., "Major Depression is Associated with Significant Diurnal Elevations in Plasma Interleukin-6 Levels, a Shift of Its Circadian Rhythm, and Loss of Physiological Complexity in Its Secretion: Clinical Implications," J Clin Endocrinol Metab 2005; 90: 2522-2530.
Amorino, G.P., Parsons, S.J., "Neuroendocrine Cells in Prostate Cancer," Crit Rev Eukaryot Gene Expr 2004; 14: 287-300 (abstract).
Anisman, H. et al., "Cytokines as a Precipitant of Depressive Illness: Animal and Human Studies," Curr. Pharm. Des. 2005; 11: 963-972.
Ashikawa, K. et al., "Piceatannol Inhibits TNF-Induced NF-κB Activation and NF-κBα Kinase and p65 Phosphorylation," J. Immunol. 2002, 6490-6497.

Bachelot, T. et al., "Prognostic value of serum levels of interleukin 6 and of serum and plasma levels of vascular endothelial growth factor in hormone-refractory metastatic breast cancer patients," Brit. J. Cancer 2003; 88: 1721-1726.

Baker, A.E. et al., "Estrogen Modulates Microglial Inflammatory Mediator Production via Interactions with Estrogen Receptor β," Endrocrinol. 2004; 145: 5021-5032.

Bardin, A. et al., "Loss of ERβ espression as a common step in estrogen-dependent tumor progression," Endocrine-Rel. Cancer 2004; 11: 537-551.

Beduschi, M.C. et al., "Alpha-Blockade Therapy for Benign Prostatic Hyperplasia: From a Nonselective to a More Selective $Alpha_{1A}$-Adrenergic Antagonist," Urology 1998; 51: 861-872.

Belcher, Scott M. and Zsarnovszky, Attila, "Estrogenic Actions in the Brain: Estrogen, Phytoestrogens, and Rapid Intracellular Signaling Mechanisms," J. Pharmacol. Exp. Therap. 2001; 299: 408-414.

Beral, V. et al., "Evidence from randomised trials on the long-term effects of hormone replacement therapy," Lancet 2002; 360: 942-944.

Chapple, C.R., "Pharmacological therapy of benign prostatic hyperplasia/lower urinary tract symptoms: an overview for the practising clinician," BJU Int. 2004; 94: 738-744.

Cheblowski, R.T. et al., "Influence of Estrogen Plus Progestin on Breast Cancer and Mammography in Healthy Postmenopausal Women," JAMA 2003; 289: 3243-3253.

Cheng, J. et al., "Expression of estrogen receptor β in prostate carcinma cells inhibits invasion and proliferation and triggers apoptosis," FEBS Lett. 2004; 566: 169-172.

Curran, E.M. et al., "Natural Killer Cells Express Estrogen Receptor-α and Estrogen Receptor-β and Can Respond to Estrogen Via a Non-Estrogen Receptor-α-Mediated Pathway," Cell. Immunol. 2001; 214: 12-20.

Dijsselbloem, N. et al., "Soy isoflavone phyto-pharmaceuticals in interleukin-6 affections Multi-purpose nutraceuticals at the crossroad of hormone replacement, anti-cancer and anti-inflammatory therapy," Biochem Pharmacol. 2004; 68: 1171-1185.

Dinarello, C.A., "Therapeutic strategies to reduce IL-1 activity in treating local and systemic inflammation," Curr. Op. Pharmacol. 2004; 4: 378-385.

Dizeyi, N. et al., "Expression of Serotonin Receptors and Role of Serotonin in Human Prostate Cancer Tissue and Cell Lines," Prostate 2004; 59: 328-336.

Donovan, J.L., "The measurement of symptoms, quality of life and sexual function," BJU Int. 2000, 85, Suppl. 1:10-19 (abstract).

Drachenberg, Darrel E. et al., "Circulating Levels of Interleukin-6 in Patients With Hormone Refractory Prostate Cancer," Prostate 1999; 41: 127-133.

Dunn, C.J. et al., "Tamsulosin: a review of its pharmacology and therapeutic efficacy in the management of lower urinary tract symptoms," Drugs Aging 2002; 19: 135-161 (bstract).

Rote Liste Service GMBH (Ed.): "Rote Liste", 2002, Editio Cantor Verlag, Aulendorf, XP002379296, Eintrag 760001 "Phytoestrol N", p. 76 001.

Sabichi A L et al: "COX-2 inhibitors and other nonsteroidal anti-inflammatory drugs in genitourinary cancer" Seminars in Oncology 2004 United States, vol. 31, No. Suppl. 7, 2004, pp. 36-44, XP009066086, ISSN: 0093-7754, p. 38.

Matsuda, H. et al., "Phytoestrogens from the Roots of Polygonum cuspidatum (*Polygonaceae*): Structure-Requirement of Hydroxyanthraquinones for Estrogenic Activity". Bioorganic & Medicinal Chemistry Letters, 11 1839-1842 , (2001).

Babu, K.S., et al.: "Yeast and mammalian a-Glucosidase Inhibitory Constituents From Himalayan Rhubarb Rheumemodi Wall.ex Meisson"> Bioorganic & Medicinal Chemistry Letters, 14 (2004) 3841-3845.

WO-Form PCT/IPEA/409—English translation of International Preliminary Report on Patentability issued in PCT/EP06/000955, Dec. 19, 2007, Heger, Peter et al.

WO-Form PCT/IPEA/409—English translation of International Preliminary Report on Patentability issued in PCT/EP06/000951, Dec. 19, 2007, Heger, Peter et al.

\* cited by examiner

USE OF AN ACTIVE INGREDIENT COMBINATION THAT CONTAINS HYDROXYSTILBENE FOR PREVENTING AND/OR TREATING DISEASES

This application is the U.S. national phase application, pursuant to 35 U.S.C. §371, of PCT international application Ser. No. PCT/EP2006/000951, filed Feb. 3, 2006, designating the United States and published in German on Aug. 10, 2006 as publication WO 2006/082068 A1, which claims priority to German application Ser. Nos. DE 10 2005 005 268.1, filed Feb. 4, 2005, DE 10 2005 005 270.3, filed Feb. 4, 2005, DE 10 2005 005 271.1, filed Feb. 4, 2005, DE 10 2005 005 273.8, filed Feb. 4, 2005, DE 10 2005 005 274.6, filed Feb. 4, 2005, DE 10 2005 005 275.4, filed Feb. 4, 2005, DE 10 2005 005 276.2, filed Feb. 4, 2005 and DE 10 2005 023 164.0, filed May 19, 2005. The entire contents of the aforementioned patent applications are incorporated herein by this reference.

The invention relates to the use of hydroxystilbene-containing active ingredients for preventing and/or treating disorders whose development and/or progression is associated with an elevated serum IL-6 level and/or whose development and/or progression can be treated by administration of a selective estrogen receptor β (ERβ) agonist. The invention relates in particular to the treatment of depression, anxiety, migraine, chronic inflammatory disorders, the chemoprevention of tumorigenesis and/or inhibition of tumor progression in cases of endocrine-dependent and -independent tumors, and for treating prostate cancer and/or LUTS (lower urinary tract symptoms).

BACKGROUND OF THE INVENTION

1. General

Important key factors in neurovegetative disorders such as depression and migraine, in chronic inflammatory disorders, in prostate hyperplasia and in tumorigenesis and tumor progression are the release of proinflammatory or procarcinogenic cytokines, and sub-sequent activation of NF-κB-mediated gene expression followed by a series of second messengers which lead to the development of these disorders or promote progression thereof. For example, large amounts of TNF-α, interleukin-1 (IL-1) and IL-6 are produced as potent proinflammatory and procarcinogenic cytokines by macrophages and many other cells (Long & Gardam, CMAJ 2003; 168: 1153-1156; Dinarello, Curr. Op. Pharmacol. 2004; 4: 378-385).

In addition to the increased cytokine production, it is suggested that the derangements in the production of neurotransmitters such as, for example, serotonin and dopamine are responsible both for migraine and depression and for tumor growth of various organs and tissues (Gilbert. Eur J Cancer Prev 1997; 6: 269-276; Spinelli. Clin Obstet Gynecol 2004; 47: 428-436; Amorino & Parsons. Crit. Rev Eukaryot Gene Expr 2004; 14: 287-300; Dizeyi et al. Prostate 2004; 59: 328-336; Siddiqui et al. Oncol Rep 2005; 14: 1593-1597).

An important regulator of neurovegetative processes and inducer of anti-inflammatory mechanisms in humans is estrogen. It has been shown in particular that an estrogen deficiency promotes the response of cells to cytokines by upregulating the number of cytokine receptors and cofactors of the action of cytokines, and thus further enhancing the effects of the increase in cytokines. In contrast thereto, it has been observed that in particular the serum-IL-6 levels are lower in postmenopausal women receiving hormone replacement therapy (HRT) (Pfeilschifter et al, Endocrine Rev. 2002; 23: 90-119). Estrogen is thus a decisive negative regulator of IL-6, and its downregulation is impaired when estrogen levels fall. In addition, estrogens improve the neurotransmitter status through changes in the hormones of the hypothalamus-hypophases axis.

Central to future therapies regulating both cytokine production and neurotransmitter production are, as important control elements, the estrogen receptors α (ERα) and β (ERβ). Estrogens regulate gene expression by binding to these nuclear receptor proteins and thus control many processes involved in development, differentiation and homeostasis in mammals (Kuiper et al., Proc. Natl. Acad. Sci. USA, 1996; 93: 5925-5930). The two receptors exhibit only partial structural similarities and their different biological functions can be explained on the basis of considerable differences in the N-terminal domain and in the ligand-binding domain (Kuiper et al., Proc. Natl. Acad. Sci. USA, 1996; 93: 5925-5930; Enmark et al., J. Clin. Endocrinol. Metab. 1997; 82: 4258-4265). In particular, the function of ERβ is only partly elucidated.

2. Chronic Inflammatory Disorders and Migraine

During the development of selective estrogen receptor β (ERβ) agonists, a significant advantageous effect of one of the investigated compounds in chronic inflammatory bowel disorders was observed in animal models (Harris et al., Endocrinol. 2003; 144: 4241-4249). Daily oral doses of 1 mg/kg of the ERβ agonist eliminated chronic diarrhea and intestinal lesions in rats. Inflammatory infiltrates were reduced and the integrity of the intestinal mucosa was restored. The severity of the disorder was reduced by 50-60%.

In studies on the Lewis rat model for adjuvant-induced arthritis, a significant improvement in the arthritis was likewise observed (Harris et al., Endocrinol. 2003; 144: 4241-4249). Inflammatory cell infiltrates were decreased, fibroblast hyperplasia was reduced and the proliferative pannus reaction was eliminated.

A study by the same research group (Harris et al. Hum. Reprod. 2005; 20: 936-941) in an endometriosis model in mice implanted with human endometrium showed a complete remission of the lesions through the ERβ agonist. This was presumably caused by an ERβ-mediated activation of immune cells which express ERβ(Curran et al., Cell. Immunol. 2001; 214: 12-20, Stygar et al., Mol. Hum. Reprod. 2001; 7: 881-886, Henderson et al., J. Clin. Endocrinol. Metab. 2003; 88: 440-449, Vegeto et al., J. Neurosci. 2001; 21: 1809-1818) which then eliminated the inflamed tissue by apoptosis.

Inflammatory cytokines and inflammatory reactions are also the cause of migraine. Cytokines stimulate the inducible NO synthase (iNOS) in the dura mater, a pain-sensitive intracranial tissue, thus producing large amounts of nitric oxide (NO) (Reuter et al., Ann Neurol 2002; 51: 507-516). Administration of an NOS inhibitor thus leads to a significant reduction in the headaches during an acute attack in two thirds of the patients. In addition, there is an increase in the level of the cytokines interleukin (IL)-1β and IL-6 and of reactive oxygen species owing to oxidative stress. These cytokines potentiate iNOS expression and thus NO production (Reuter et al, Ann Neurol 2002; 51: 507-516).

It has been possible to show that estrogens interact with the binding of the NF-κB/RelA protein at appropriate sites in the promoter, for example of IL-6 and iNOS, and thus inhibit their gene expression (Stein et al., Mol Cell Biol. 1995; 15: 4971-4979; Galien et al., Nucleic Acids Res. 1997; 25: 2424-2429; Wen et al., Brain Res. 2004; 1008: 147-154). Activation of ERβ in particular appears to be responsible for suppressing the production of mediators of inflammation in microglial cells in certain regions of the brain (Baker et al., Endocrinol. 2004; 145: 5021-5032).

Activation of ERβ by ERβ-selective ligands and subsequent inhibition of cytokine production might thus be a crucial mechanism for inhibiting processes associated with chronic inflammatory disorders and with migraine.

3. Depression and Anxiety

The anxiolytic and antidepressant effects of estrogen are also mediated by ERβ. An estrogen treatment increases the activity of the dopaminergic and serotoninergic system and alleviates psychological symptoms in humans. Ovariectomized ERβ-knockout mice showed increased anxiety and significantly reduced dopamine and serotonin levels compared with the wild-type mice. By contrast, an increase in anxiety appears to be mediated by ERα (Imwalle et al. Lack of functional Estrogen receptor β influences anxiety behavior and serotonin content in female mice. Physiology & Behavior 2005; 84: 157-163).

In the forced-swimming test, a model for investigating the antidepressant effect of medicaments, ovariectomized ERβ-k.o. mice showed an increased immobility, which could not be abolished even by estradiol administration. It was therefore postulated that substances which selectively activate ERβ are able to reduce anxiety and depression (Imwalle et al. 2005; Lund et al. Novel Actions of Estrogen Receptor Beta on Anxiety-Related Behaviors. Endocrinology 2005; 146: 797-807; Rocha et al. 17β-Estradiol-induced antidepressant-like effect in the forced swim test is absent in estrogen receptor-β knockout (BERKO) mice. Psychopharmacology 2005, 179: 637-643). It was in fact possible to reduce drastically the anxiety of the animals in the rat model by administering ERβ-selective activators such as, for example, diarylpropionitrile (DPN) or coumestrol (Walf & Frye. ERβ-selective estrogen receptor modulators produce antianxiety behavior when administered systemically to ovariectomized rats. Neuropsychopharmacology 2005; 1-12).

Proinflammatory cytokines, especially IL-6, also play an important part in depression (Miller & O'Callaghan: Depression, cytokines, and glial function. Metab Clin Exp 2005; 54: 33-38; Alesci et al.: Major depression is associated with significant diurnal elevations in plasma interleukin-6 levels, a shift of ist circadian rhythm, and loss of physiological complexity in ist secretion: clinical implications. J Clin Endocrinol Metab 2005; 90: 2522-2530; Motivala et al.: Inflammatory markers and sleep disturbande in major depression. Psychosom Med 2005; 67: 187-194; Anisman et al.: Cytokines as a precipitant of depressive illness: animal and human studies. Curr. Pharm. Des. 2005; 11: 963-972). It was shown in animal models that treatment with, for example, IL-6 induced pathological behavior and symptoms of depression which were treatable only by chronic treatment with antidepressants (Anisman et al. 2005). Immunotherapy with IL-2 or TNF-α leads to strong symptoms of depression in patients, which are attributed to the elevated IL-6 levels.

It was of interest to find in patients with depression that treatment with antidepressants did not lead to a reduction in the cytokine levels, in particular not of IL-6 (Anisman et al. 2005, loc. cit.). This means that although antidepressants reduce or mask the symptoms, the triggers remain in existence. This may be a reason for the frequent relapses during therapy with the antidepressants normally employed.

4. Tumorigenesis and Tumor Progression

IL-6 is additionally an important key factor in tumorigenesis. Elevated IL-6 plasma levels have been measurable in a wide variety of neoplastic diseases and could be reduced only by chemotherapy. Tumor cells themselves produce IL-6 which, in an autocrine mechanism, stimulates the growth and migration of the cells. IL-6 is therefore regarded as responsible for the alterations of the proliferation and removal of inhibition of differentiation in many malignant tumors (breast, prostate, pulmonary lymphoma, ovaries, gastrointestinal tract, kidneys). In addition, it also appears to be responsible for the chemoresistance of solid and hematopoietic tumors (for review, see: Dijsselbloem et al.: Soy isoflavone phytopharmaceuticals in interleukin-6 affections. Multi-purpose nutraceuticals at the crossroad of hormone replacement, anti-cancer and anti-inflammatory therapy. Biochem Pharmacol. 2004; 68:1171-1185).

In particular, IL-6 is regarded as a prognostic marker in patients with hormone-independent tumors such as, for example, prostate carcinoma (Drachenberg et al.: Circulating levels of interleukin-6 in patients with hormone refractory prostate cancer. Prostate 1999; 41:127-133) or breast carcinoma (Bachelot et al.: Prognostic value of serum levels of interleukin 6 and of serum and plasma levels of vascular endothelial growth factor in hormone-refractory metastatic breast cancer patients. Brit. J. Cancer 2001; 88:1721-1726). High IL-6 serum levels associated with these tumors correlate with a shorter life expectancy.

This shows that a reduction in the IL-6 levels can make a crucial contribution to improving the chances of survival and the freedom from remissions both for endocrine-dependent and -independent tumors. Therapy to date has used the conventional nonspecific chemotherapeutic agents and is known to be characterized by extensive side effects and intolerance (Lehrbuch Mutschler et al.: Arzneimittelwirkungen). A specific anti-IL-6 tumor therapy with a monoclonal antibody against IL-6 has been carried out to reduce IL-6 levels in several clinical studies (Trikha et al.: Targeted anti-interleukin-6 monoclonal antibody therapy for cancer: a review of the rationale and clinical evidence. Clin Cancer Res. 2003; 9:4653-4665). However, a disadvantage which emerged was that on use of the murine anti-IL-6 antibody, 20% of the patients produced antibodies against the Fc part of the mouse antibody, and the latter was thus eliminated very rapidly. It was thus no longer possible to achieve inhibition of the IL-6 effect in vivo.

The aim therefore is to find medicinal substances which, even after prolonged intake, effect a reduction in IL-6 levels and thus prevent tumor progression or remission without causing side effects or chemoresistance.

As already mentioned, expression of IL-6 is suppressed by estrogen via an ER-dependent mechanism. This correlates with the observation that the IL-6 concentrations were distinctly higher in those breast carcinomas which were ER-negative and not amenable to tamoxifen therapy or adjuvant chemotherapy (Jiang et al.: Reduction in serum IL-6 after vaccination of breast cancer patients with tumour-associated antigens is related to estrogen receptor status. Cytokine 2000; 12:458-465).

It has been proposed on the basis of several clinical and experimental studies that an imbalance in the expression of ERα and ERβ might represent as common feature a critical step in the progression of estrogen-dependent tumors. The balance between the ERα and ERβ receptor appears to be of essential importance for maintaining a normal cellular function inasmuch as ERβ acts as negative regulator of the ERα-mediated signal transmission which is responsible for the proliferation. This is also proved by investigations on ERβ-knockout mice. Overexpression of ERα in these mice results in a hyperproliferative uterus and leads to ovarian carcinogenesis (Frasor et al., Endocrinol. 2003; 144: 3159-3166).

The ERα-mediated mitogenic effects of estrogen also in humans are attributed with a critical role in the development and progression of human breast, endometrial and ovarian cancer. This has recently been shown by the results of large prospective studies on menopausal women (Beral et al., Lancet 2002; 360: 942-944; Cheblowski et al., JAMA 2003; 289: 3243-3253; Writing Group for the Women's Health Initiative Investigators, JAMA 2002; 288: 321-333; Million Women Study Collaborators; Lancet 2003; 362: 419-427).

It is postulated that the antiproliferative effect of ERβ is mediated by interactions with various proliferative events, leading to a protective effect against ERα-induced hyperproliferation. In particular, inhibition of the antiapoptotic gene expression, induction of proapoptotic gene expression and inhibition of ERα-induced cell proliferation are suggested (Bardin et al., Endocrine-Rel. Cancer 2004; 299: 408-414).

It has been observed in various organs and tissues, such as breast, ovaries, uterus and large bowel, that under conditions of a decrease in ERβ expression (e.g. associated with hyperplasia, neoplastic lesions) there is an uncontrolled cellular proliferation owing to ERα activation, leading to a tumorigenic status (Bardin et al., Endocrine-Rel. Cancer 2004; 11: 537-551). Thus, a selective activation of ERβ might be of therapeutic importance in the prevention and/or treatment of estrogen-dependent tumors, for example in the breast, the ovaries, the uterus, the prostate and the colon.

Current treatment strategies for breast cancer in the early stage include the selective estrogen receptor modulator (SERM) tamoxifen which, however, as ER antagonist, is effective only for ER-positive breast cancer but shows no effect for ER-negative breast cancer (Park & Jordan, Trends Mol. Medicine. 2002; 8: 82-88; Hanstein et al., Eur. J. Endocrinol. 2004; 150: 243-255). It has additionally been observed that chronic treatment with tamoxifen induces endometrial cancer owing to its ERα agonistic activity (Stygar et al., Reprod. Biol. Endocrinol. 2003; 1: 40). Tamoxifen may therefore not be used for longer than two years for postoperative management.

It is true that estrogens have an important function in the framework of normal growth, differentiation and development of the prostate. However, estrogens are, in synergism with allergens, effective inducers of aberrant growth and neoplastic transformation of the prostate. ERα is expressed mainly in the stroma compartments of the prostate and in the bone metastases and the metastases in the regional lymph nodes, and is therefore presumed to be involved in the pathogenesis of prostate cancer.

By contrast, ERβ suppresses an AR-mediated hyperproliferation and promotes the differentiation of prostate epithelial cells (Imamov et al., N. Engl. J. Med. 2004; 351: 2773-2774). It has also been possible to show this on older ERβ knockout mice which, in contrast to the wild-type mice, developed prostate hyperplasia (Krege et al., Proc. Natl. Acad. Sci. 1998; 95: 15677-15682). It has been possible to show in several studies that ERβ is downregulated during prostate carcinogenesis and thus an ERβ-mediated inhibition of the invasion and apoptosis of the tumor cells cannot be maintained to a sufficient extent (Weihua et al., Proc. Natl. Acad. Sci. 2002; 99: 13589-13594; Cheng et al., FEBS Lett. 2004; 566: 169-172). It is of interest that the endogenous ligand for ERβ in the prostate is not estradiol but 5α-androstane-3β,17β-diol (3βa-diol or 3β-androstanediol), which is formed from dihydrotestosterone (DHT) and thus limits the effect of DHT (Weihua et al., Proc. Natl. Acad. Sci. 2002; 99: 13589-13594). Disturbance of this balance between AR and ERβ activation by, for example, inhibiting by the 5-α-reduktase inhibitor finasteride the formation of DHT from testosterone, and thus also the production of 3βadiol, stops ERβ-mediated differentiation of the prostate epithelium. This mechanism might be responsible for the higher rate of undifferentiated tumors in the finasteride group of the prostate cancer prevention trial (Weihua et al. 2002). It has additionally been shown recently that 5α-androstane-3β,17β-diol inhibits through the activation of ERβ the migration of prostate carcinoma cells and thus prevents cell invasion and metastasis (Guerini et al. Cancer Res 2005; 65:5445-5453). It therefore appears to be worthwhile for prostate carcinoma prevention or therapy to combine fenasteride with an ERβ activator for those patients in whom ERβ is still detectable in the prostate carcinoma.

The rate of proliferation of prostate cancer cells is rather low and consequently the efficiency of chemotherapy for the treatment of prostate cancer is low. Current treatment strategies include antiandrogens which represent either steroid derivatives such as cyproterone acetate, or non-steroidal bicalutamide or flutamide. However, these active ingredients are effective only for hormone-sensitive prostate cancer. The commonest side effects of these active ingredients are gynacomastia, cardiovascular disorders, fatigue, loss of appetite, reduced libido and spermatogenesis, and increased hepatotoxicity.

An increased production of IL-6 is also a further important factor for the development of prostate cancer (George et al. Clin Cancer Res 2005, 11: 1815-1820). IL-6 activates the androgen receptor and thus leads to hyperproliferation of the prostate epithelium. An elevated IL-6 level is also regarded as a prognostic marker in hormone-independent prostate tumors. Therapy with anti-IL-6 antibodies has therefore been regarded as promising to reduce the morbidity. However, this therapy of prostate carcinoma is still in the development stage and is moreover associated with high costs.

In addition, both IL-6 and endocrine changes play an important part in the development of benign prostate hyperplasia and of lower urinary tract symptoms (LUTS; Konig et al. Prostate. 2004, 58: 121-129; Donovan J. L., BJU Int. 2000, 85, Suppl. 1: 10-19). LUTS are frequently associated with benign prostate obstruction (BPO) and secondarily with benign prostate hyperplasia (BPH, Chapple, C. R., BJU Int. 2004; 94: 738-744). Dihydrotestosterone and estradiol are key factors in this disorder. 5-Alpha-reductase is the enzyme responsible for converting testosterone into 5-alpha-dihydrotestosterone (DHT). It is thus primarily DHT, and not testosterone, which is responsible for prostate development through activation of the AR. The conventional treatment of LUTS is focused on 5-alpha-reductase inhibitors, e.g. finasteride, and alpha, blockers, e.g. tamsulosin.

Typical side effects such as reduced libido and spermatogenesis mean, however, that patients' compliance with finasteride is low (Peters & Sorkin, Drugs 1993; 46: 177-208). In addition, finasteride reduces the level of prostate-specific antigen (PSA) and thus blocks early diagnosis of prostate carcinoma (Peters & Sorkin, Drugs 1993; 46: 177-208). Among the alpha, blockers, tamsulosin is specifically directed at the adrenergic alpha$_{1A}$ receptor subtype (Beduschi et al., Urology 1998; 51: 861-872; Dunn et al., Drugs Aging 2002; 19: 135-161). Although tamsulosin causes less dizziness and other cardiovascular side effects than other alpha, blockers, there is nevertheless a high risk of abnormal ejaculation, such as, for example, retrograde ejaculation, reduced ejaculation volume or complete absence of ejaculation (Lepor, Urol. 1998; 51 (6): 892-900).

There is thus a need for novel active ingredients for treating endocrine-dependent and endocrine-independent tumors such as, for example, breast and prostate cancer, or hyperplasias such as, for example, LUTS, and these active ingredients ought not to show any ERα-activating potential in other tissues and organs. One way would be to activate ERβ as the natural antagonist of ERα. Selective activators of ERβ which do not display the described side effects, especially on chronic use, are therefore of interest.

Naturally occurring phytoestrogens such as the soybean flavonoids genistein and daidzein, or the flavonoids coumestrol show a certain preference for ERβ. However, they also activate ERα in vivo (Kuiper et al., Endocrinol. 1997, 138: 863-870; Belcher & Zsarnovszky, J. Pharmacol. Exp. Therap. 2001; 299: 408-414), so that chronic treatment, for example with soybean-containing products in the effective doses, might display a certain carcinogenic potential. After use of a very high-dose soybean product for menopausal symptoms for 5 years, endometrial hyperplasia was observed and is attributable to activation of ERα in this tissue (Unfer. Fertil Steril 2004; 82: 145-148).

5. Further Prior Art

Since 1993, a dry extract of roots of *Rheum rhaponticum* has been on the market in Germany under the name Extrakt *Rheum rhaponticum* (ERr 731®) (proprietary name Phytoestrol® N) for follicle hormone replacement therapy, for example for treating women with menopausal symptoms, juvenile oligomenorrhea and dysmenorrhea, primary and secondary amenorrhea, and endometritis. The constituents of the specific ERr 731® extract are rhaponticin, deoxyrhaponticin, rhapontigenin and deoxyrhapontigenin (table 1).

TABLE 1

Composition of the extract ERr 731 ®

| Hydroxystilbene | Chemical name | CAS No. |
|---|---|---|
| Rhaponticin | 3,3',5-Trihydroxy-4'-methoxystilbene 3-O-β-D-glucopyranoside | 155-58-8 |
| Deoxyrhaponticin | 3',5-Dihydroxy-4'-methoxystilbene 3-O-β-D-glucopyranoside | 30197-14-9 |
| Rhapontigenin (trans-Rhapontigenin) | 3,3',5-Trihydroxy-4'-methoxystilbene | 500-65-2 |
| Deoxyrhapontigenin | 3',5-Dihydroxy-4'-methoxystilbene | 33626-08-3 |

All of the constituents of ERr 731® belong to the group of hydroxystilbenes. Representatives of this group have the following general formula:

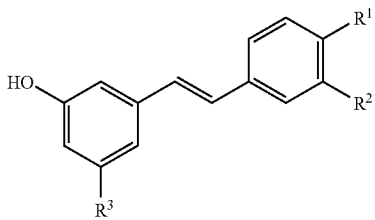

|  | R¹ | R² | R³ |
|---|---|---|---|
| Resveratrol | OH | H | OH |
| Rhaponticin | OCH₃ | OH | O-Glc |
| Deoxyrhaponticin | OCH₃ | H | O-Glc |
| Rhapontigenin | OCH₃ | OH | OH |
| Deoxyrhapontigenin | OCH₃ | H | OH |
| Astringin | OH | OH | O-Glc |
| Piceatannol (astringenin) | OH | OH | OH |

Several studies have shown that the number and position of the free hydroxy and methoxy groups strongly influences the biological activity of the hydroxystilbenes (Kageura et al. Bioorganic & Medicinal Chemistry 9 (2001) 1887-1893, Matsuda et al. Biol. Pharm. Bull. 2001 (24(3) 264-267, Roberti et al. J. Med. Chem. 2003, 46, 3546-3554). The pharmacological effect of the hydroxystilbenes is moreover dependent on the presence of a glucose group (Park et al. Arch. Pharm. Res. 2002, 25(4), 528-533).

There has been only inadequate investigation of whether, and to which metabolites, the constituents of ERr 731® are degraded in the body for example after oral administration. Thus, it is merely known from investigations on the antithrombotic and antiallergic activity of rhaponticin-containing extracts from rhizoma rhei that rhaponticin is degraded by bacteria of the human intestinal tract to rhapontigenin (Park et al, Arch. Pharm. Res. 2002, 25 (4), 528-533). Metabolism of rhaponticin to piceatannol or of deoxyrhaponticin to resveratrol has not been observed to date.

Morris et al. describe in The Prostate 2002, 52, 319-329, the apoptotic effect of pure resveratrol on hormone-sensitive and -insensitive prostate cancer cells and suggest that chronic exposure through intake of low resveratrol concentrations with the diet might inhibit the development of prostate cancer. An active preventive treatment by administering a resveratrol-containing composition is not proposed.

Ashikawa et al. describe in J. Immunol. 2002, 6490-6497 the inhibitory effect of piceatannol on the transcription factor NF-κB. The authors regard this as an explanation for an antitumor effect of piceatannol. Rhaponticin was by contrast inactive in these tests. Use of piceatannol for treating prostate cancer or LUTS is not proposed.

Roberti et al. describe in J. Med. Chem. 2003, 46, 3546-3554, the apoptotic effect of resveratrol and analogues on HL60 leukemia cells. The most effective analogues in this connection were certain derivatives with the cis configuration.

Gao et al. describe in The Prostate 2004 59, 214-225, the modulation by resveratrol of AR-dependent signalling pathways which are thought to be associated with prostate cancer. Depending on the concentration, an increase or inhibition of AR-dependent gene expression was observed.

Aggarwal et al. describe in a review article (Anticancer Research, 24, 2004) the role of resveratrol in the prevention and treatment of various types of cancer, including prostate cancer.

FR 2 835 185 describes a complex rhubarb extract obtainable from rhizomes of *Rheum rhaponticum*, which is said to be characterized in that it comprises at least 50% hydroxystilbenes, with at least 50% of these hydroxystilbenes consisting of rhaponticin, deoxyrhaponticin, astrangin and piceatannol. A preferred extract comprises 15-50% by weight rhaponticin, 10-35% by weight deoxyrhaponticin, 5-10% by weight astrangin and 0.1-3% by weight piceatannol. This extract is, as illustrated in the examples, prepared by hydroalcoholic extraction of rhizomes of *Rheum rhaponticum*. The total content of rhaponticin and deoxyrhaponticin which can be obtained thereby is only 76% by weight. The content of astrangin comprises 11% by weight, the content of piceatannol comprises 3% by weight, and the content of anthracenosides comprises 0.5% by weight. In addition thereto, this extract appears to comprise about 10% by weight further undefined constituents. It is additionally asserted in FR 2 835 185 that the specific extract therein has, as a result of alleged synergistic effects of the various ingredients of the extract, biological properties which are considerably superior to the effect of the individual hydroxystilbenes, especially those effects which the ingredients described therein are said to have individually. The extract described therein is alleged to have antioxidant, antitumor, antiinflammatory and estrogenic properties. However, in fact, FR 2 835 185 does not provide a verifiable technical teaching for the asserted pharmacological usability, to say nothing of the asserted synergistic effect of the complex drug extract described therein. The experimental section describes merely individual formulation examples of capsules, tablets or creams. In particular, experimental data proving the alleged usability for the treatment of disorders connected with free radicals, such as, for example, accelerated aging, cancer, arteriosclerosis, wrinkles, inflammatory phenomena and the like, are completely lacking. The asserted suitability of a combination of the rhubarb extract described therein with a hop extract rich in prenyl flavonoids for the treatment of diseases standing with free radicals and/or for the treatment of hormonal imbalance such as amenorrhea, menopause, hot flushes etc., is not proved by any data either. It is moreover entirely unclear which of the components actually present in the extract described therein (rhaponticin, deoxyrhaponticin, astrangin, piceatannol, anthracenosides, and the unanalyzed constituents present in a content of 10%) contribute to the asserted pharmacological activity or, where appropriate, are in fact absolutely necessary for the asserted synergism. The actual disclosure of FR 2 835 185 should therefore be restricted to the preparation of a specific, complex rhubarb extract by hydroalcoholic extraction of rhizomes of *Rheum rhaponticum* and the preparation of specific hydroxystilbene derivatives, and the production of various pharmaceutical formulations.

SUMMARY OF THE INVENTION

The present invention was therefore based on the object of finding a new way of pre-venting and/or treating disorders whose development and/or progression is associated with an elevated serum IL-6 level and/or whose development and/or progression can be treated by administration of a selective estrogen receptor 1 (ERβ) agonist.

This object has surprisingly been achieved by the use of a hydroxystilbene-containing active ingredient combination as defined in the appended claims for producing a pharmaceutical composition which is surprisingly advantageously suitable for the treatment of the abovementioned group of disorders.

The present invention is based on the identification of a novel mode of action of active ingredients and active ingredient combinations of the invention, such as, in particular, of the dry extract ERr 731® and its ingredients and metabolites.

DESCRIPTION OF THE FIGURES

FIG. 7 shows the antiandrogenic activity of various hydroxystilbenes in an androgen receptor-expressing yeast cell system.

DETAILED DESCRIPTION OF THE INVENTION

1. Preferred Aspects of the Invention

Figure 1:
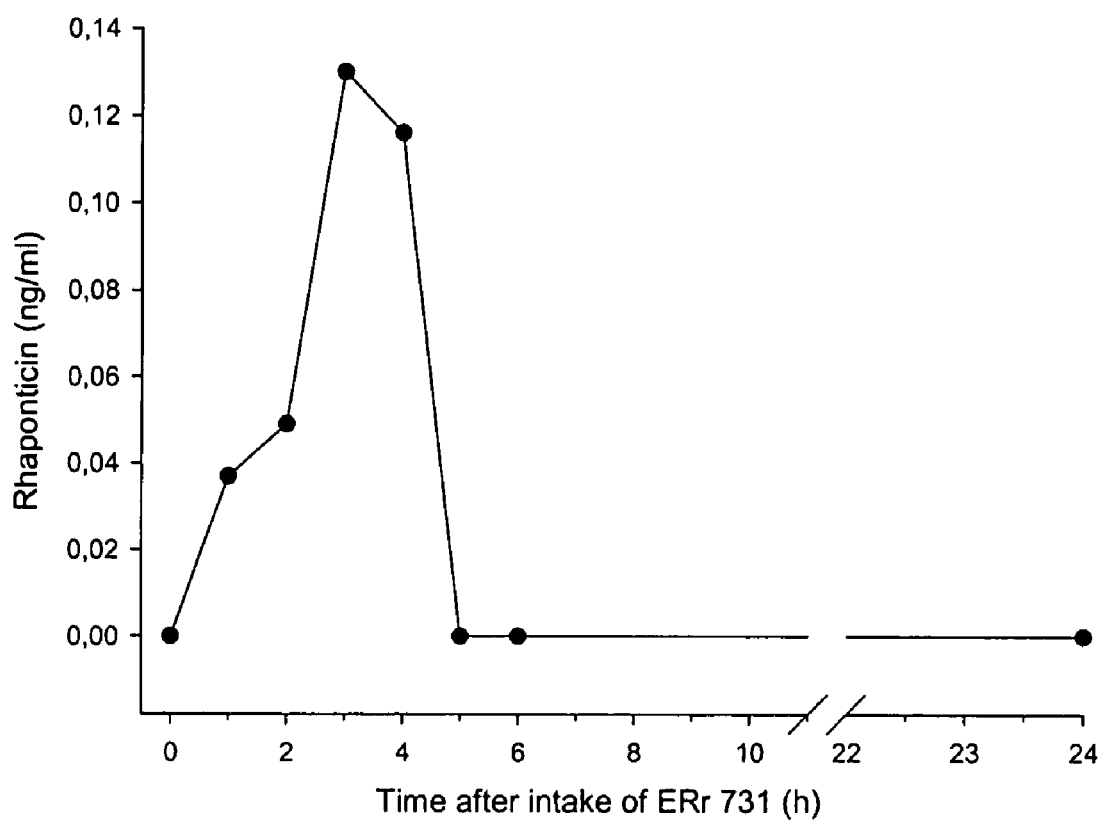
FIG. 1 shows the result of a pharmacokinetic investigation on the ingredient rhaponticin in ERr 731® in the blood of a female subject after oral administration of ERr 731®. Rhaponticin was detectable in the blood, but not rhapontigenin. Likewise, the metabolite thereof piceatannol was undetectable in the blood under the experimental conditions.

A first aspect of the invention relates to the use of a hydroxystilbene-containing active ingredient or of a hydroxystilbene-containing active ingredient combination selected from resveratrol and piceatannol prodrugs (precursors), such as, in particular, rhaponticin, deoxyrhaponticin, rhapontigenin, deoxyrhapontigenin and astrangin; and resveratrol and piceatannol; and the stereoisomeric forms thereof, especially cis and trans forms, in each case in the form of their salts or in the phenol form, or combinations of these compounds for producing a composition for the treatment of disorders.

The invention relates in particular to the use of a hydroxystilbene-containing active ingredient combination comprising at least two compounds selected from precursors of resveratrol and piceatannol such as, in particular, rhaponticin, deoxyrhaponticin, rhapontigenin, deoxyrhapontigenin and astrangin; and the stereoisomeric forms thereof, in each case in the form of their salts or in the phenol form, or functional derivatives thereof, for producing a composition for preventing and/or treating disorders whose development and/or progression is associated with an elevated serum IL-6 level and/or whose development and/or progression can be treated by administration of a selective estrogen receptor β (ERβ) agonist.

A normal, i.e. not pathologically elevated, serum IL-6 level is influenced by factors such as age and gender. However, a baseline value of about 0 to 2 pg/ml of serum can be assumed for the IL-6 level.

The invention also relates to the use of a hydroxystilbene-containing active ingredient combination comprising at least two compounds selected from precursors of resveratrol and piceatannol such as, in particular, rhaponticin, deoxyrhaponticin, rhapontigenin, deoxyrhapontigenin and astrangin; and the stereoisomeric forms thereof; in each case in the form of their salts or in the phenol form, or functional derivatives thereof, for producing a composition for the a. prevention and/or treatment of neurovegetative disorders such as, in particular, depression, anxiety, and migraine, b. prevention and/or treatment of chronic inflammatory disorders, c. chemoprevention of tumorigenesis and/or inhibition of tumor progression for endocrine-dependent and/or -independent tumors, or d. treatment of prostate cancer and/or of LUTS.

The active ingredient combination used according to the invention is characterized in particular by (1) a total hydroxystilbene content of more than 90% by weight; and/or (2) a total content of glycosidic precursors of resveratrol and piceatannol of more than 76% by weight, and/or (3) an aglycone content of less than 5% by weight; and/or (4) a content of less than 0.5% by weight of anthraquinone and/or anthraquinoids, where the percentage data are in each case based on the dry weight of the active ingredient combination.

Compositions of the invention are in this connection selected in particular from medicaments such as, for example, homeopathic remedies, other medicinal plant preparations, dietary supplements, dietetic food products.

Resveratrol and piceatannol prodrugs in the sense of the invention are in particular substances which can be converted, partly or completely, into resveratrol and/or piceatannol in vivo, such as, for example, in humans and/or another mammal, such as, for example, dog. Possibilities in this connection are sugar-containing (glycones, glycosides) or sugar-free (aglycones) natural or synthetic "precursors" of resveratrol or piceatannol. Typical examples of sugar-containing precursors include rhaponticin, astringin and deoxyrhaponticin. Typical examples of sugar-free precursors include rhapontigenin and deoxyrhapontigenin. The terms "prodrug" or "precursor" are, however, not to be understood as functional restriction in the context of the invention. As proven by the experimental results described hereinafter, in particular the "precursors" of the invention per se display advantageous pharmacological effects.

The active ingredients are preferably substantially present in the trans form. Salts are in particular the alkali metal and alkaline earth metal phenolates of the above compounds which have one or more free phenolic hydroxyl groups. If a plurality of hydroxyl groups is present, these can be partly or completely in the salt form.

The active ingredient to be employed according to the invention or the active ingredient combination is in this connection chemically synthesized or, in particular, can be isolated from natural or recombinant plants. The resulting plant extracts or individual components thereof can also be subjected to derivatization reactions in order to obtain so-called functional derivatives. These are in particular derivatives which can be converted back in the human or animal body, after administration, into the underivatized starting compound again. Mention should be made in particular of ethers and ester derivatives of the compounds used according to the invention. It is moreover possible for individual ones or all of the etherifiable or esterifiable groups in a molecule (especially the phenolic and glucosidic hydroxy groups) to be derivatized. Examples of suitable derivatives and their preparation are described for example in FR 2 835 185, which is incorporated herein by reference. Thus, mention may be made of: esters of saturated or unsaturated, aliphatic or aromatic carboxylic acids having up to 25 carbon atoms, such as 1 to 25 carbon atoms, such as, for example, saturated $C_6$-$C_{22}$ fatty acids (such as, for example, saturated unbranched fatty acids selected from caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid); or silyl ethers, where the silicon atom carries three identical or different, straight-chain or branched, saturated or unsaturated hydrocarbon radicals having up to 20 carbon atoms, such as, for example, $C_1$-$C_{20}$ alkyl or $C_2$-$C_{20}$ alkenyl.

An active ingredient combination of at least two of the abovementioned compounds is preferably employed, such as, for example, 2, 3, 4, 5, 6, 7 or 8 individual compounds, where the group of resveratrol precursors (especially deoxyrhaponticin and deoxyrhapontigenin) and of piceatannol precursors (especially rhaponticin and rhapontigenin) is represented in each case by one compound.

In a preferred embodiment, the active ingredient or the active ingredient combination is obtainable from plants which are selected from natural plants and plants which have been modified by breeding or recombinant, genetically modified plants, which have a content of at least one of the desired ingredients which is higher by comparison with the corresponding unmodified plant. These plants are in particular selected from plant of the genus *Rheum* spp., *Astragalus* spp., *Cassia* spp. or *Picea* spp. or active ingredient-containing plant parts. Nonlimiting examples of suitable species of these genera are *Rheum undulatum, Rheum palmatum, Rheum tataricum, Rheum officinale, Rheum wittrockii, Rheum altaicum, Rheum reticulatum, Astragalus complanatus, Cassia garrettiana* and *Picea sitchensis*.

The skilled person is additionally aware that genera/species differing in provenance and differing in age (e.g. harvest at various times of the vegetation period) can be employed, in turn possibly influencing the nature, amount and composition of the active ingredients and mixtures which can be isolated therefrom. It is likewise possible in principle to use various plant parts, such as roots, rhizomes, leaves and/or stalks.

The active ingredient or the active ingredient combination is particularly advantageously obtainable from the roots, especially of *Rheum rhaponticum*.

In a further preferred embodiment, the active ingredient combination substantially comprises rhaponticin and deoxyrhaponticin, it being possible for the active ingredient combination substantially to comprise rhaponticin and deoxyrhaponticin in a ratio by weight of about 10:1 to 1:10, such as, for example, in a range of about 5:1 to 1:5 or 4:1 to 1:4 or 3:1 to 1:3 or 2:1 to 1:2 or about 1:1.

A further preferred active ingredient combination may comprise rhaponticin and deoxyrhaponticin, in particular in the ratios of amounts indicated above, and rhapontigenin and/or deoxyrhapontigenin. The quantitative proportion of rhapontigenin and/or deoxyrhapontigenin in the total active ingredient content may vary over a wide range and is, for example, in the range of about 0.01 to 20% by weight, in particular 0.1 to 5% by weight, based on the total active ingredient content.

Preference is further given to active ingredient combinations which have a total hydroxystilbene content, in particular a total content of deoxyrhaponticin, deoxyrhapontigenin, rhaponticin and rhapontigenin, or a total content of rhaponticin and deoxyrhaponticin, of more than 90% by weight, such as, for example, 91 to 100% by weight, or 92 to 99 or 93 to 98 or 94 to 97% by weight.

In a further preferred embodiment there is use of an active ingredient combination which is substantially free of aglycone derivatives of rhaponticin and deoxyrhaponticin, such as, in particular, resveratrol and piceatannol. "Substantially free" means an aglycone content of less than 5% by weight, in particular less than 2% by weight, such as, for example, less than 1% by weight or 0.1% by weight, such as 0 to 0.05% by weight, in each case based on the total content of rhaponticin and deoxyrhaponticin.

In a further preferred embodiment an active ingredient combination used is a plant dry extract which has a high content of glycosides, in particular glycosides of the type described above. Glycosides are in particular the above-described glycosidic precursors of resveratrol and piceatannol. These are present for example in a content of from 30 to 100% by weight, 50 to 100% by weight, but preferably in contents of more than 76% by weight, such as 76 to 99% by weight or 80 to 98% by weight or 85 to 96% by weight, in each case based on the total weight of the dry extract.

Preference is further given to active ingredient combinations which have a content of less than 0.5% by weight, such as, for example, 0-0.49% by weight or 0.001 to 0.3 or 0.01 to 0.2 or 0.01 to 0.1% by weight of anthraquinone and/or anthraquinoids (in each case based on the dry weight of the active ingredient combination). Anthraquinoids are in this connection to be understood in the widest sense as substances having a basic anthraquinone structure.

A "dry extract" in the sense of the invention is one where the residual moisture content, i.e. the residual content of water and/or organic liquid (such as extractant), is less than about 5% by weight, in particular less than 2% by weight, such as, for example, 0 to 1.5% by weight or 0.1 to 0.5% by weight, in each case based on the total weight of the resulting dry extract.

Nonlimiting examples of a suitable active ingredient combination comprising the active ingredients rhaponticin, deoxyrhaponticin, rhapontigenin, deoxyrhapontigenin, are detailed below:
60-70% by weight, such as, for example, 60-66 or 62-68% by weight, rhaponticin
30-40% by weight, such as, for example, 30-36 or 31-37% by weight, deoxyrhaponticin
0-2% by weight trans-rhapontigenin and
0-2% by weight deoxyrhapontigenin;
or
50-60% by weight, such as, for example, 53-58% by weight, rhaponticin
20-30% by weight, such as, for example, 14-28% by weight, deoxyrhaponticin
5-20% by weight, such as, for example, 10-18% by weight, trans-rhapontigenin and
0-10% by weight, such as, for example, 4-10% by weight, deoxyrhapontigenin;
in each case based on the total active ingredient content and in particular on the total content of rhaponticin, deoxyrhaponticin, rhapontigenin and deoxyrhapontigenin.

The active ingredient combinations described above are particularly suitable for use for the following medical purposes:
a) prevention and/or treatment of prostate cancer and LUTS, such as benign prostate obstruction and/or benign prostate hyperplasia.
b) Prevention and/or treatment of mild to moderate depression and anxiety states, in particular treatment of mild to moderate depression and anxiety states in female menopausal or non-menopausal patients or male patients;
The degree of severity of depression and anxiety can in this connection be determined in accordance with standards acknowledged by experts, such as the HAMA anxiety scale, Beck anxiety inventory scale (BAI), Beck depression inventory scale (BDI-II) or the HAMD depression scale.
c) Prevention and/or treatment of chronic inflammatory disorders, where the inflammatory disorder is selected in particular from osteoarthritis, rheumatoid arthritis, juvenile idiopathic arthritis, psoriatic arthritis, Psoriasis vulgaris, endometriosis, bladder, urine and kidney inflammations, and inflammatory bowel disorders such as Crohn's disease and ulcerative colitis.
d) Prevention and/or treatment of endocrine-dependent tumors selected from tumors of the breast, of the ovaries, of the uterus, of the prostate and of the colon, where the endocrine-independent tumor is selected from tumors of the breast, of the ovaries, of the uterus, of the prostate and of the colon
e) Prevention and/or treatment of migraine.

The invention also relates to the use of active ingredients or combinations thereof as defined above in combination with at least one further active ingredient which is suitable for the prevention and/or treatment of one of the abovementioned disorders and differs from compounds as defined above. It is possible in particular also to combine with vitamins, minerals, further medicinal plant preparations and/or dietary supplements and/or dietetic food products.

The invention also relates to a dosage form comprising an active ingredient or an active ingredient combination as defined above in a pharmaceutically acceptable carrier.

Suitable solid dosage forms have a total active ingredient content of about 1 to 20 mg, such as, for example, 2 to 10 mg, per dose unit.

The invention relates in particular to solid dosage forms which have a sugar-free, in particular mono- or disaccharide-free, such as, for example, lactose-free, core.

Suitable solid dosage forms may be in the form of a pill, a tablet, an extrudate or granules.

Solid dosage forms in the form of a coated tablet, where appropriate with a gastro-resistant coating, are likewise suitable. Such coatings are preferably free of plasticizers such as phthalates, such as, for example, diethyl phthalate. Coating compositions suitable in particular for producing gastro-resistant, plasticizer-free coatings are selected from known natural and synthetic coating compositions (cf., for example, Voigt, Pharmazeutische Technologie, 7th edition 1993, Ullstein Mosby, Berlin). Particularly suitable coating compositions are, without being restricted thereto, shellac and cellulose derivatives such as hydroxypropylmethylcellulose derivatives such as, for example, hydroxypropylmethylcellulose acetate succinate, obtainable under the proprietary name AQOAT.

Mention should be made in particular of a solid dosage form with a total weight in the range of about 150 mg±20 mg, a core weight of 84 mg±10 mg and an active ingredient content of about 3 to 10 mg.

Further suitable solid dosage forms are those having a uniformity of active ingredient content (averaged over 10 or 20 randomly selected individual dose units) not exceeding ±5% by weight, such as, for example, ±0.1 to 4 or ±0.5 to 3 or ±1 to 2% by weight, based on the total weight of the dose unit (e.g. determined as specified in Ph. Eur. 5th edition 2005 (5.0/2.09.06.00)).

The invention further relates to a process for producing a solid dosage form where
a) the active ingredient or the active ingredient combination is mixed with the pharmaceutically acceptable carrier; and
b) the mixture is consolidated to give the active ingredient core.

For this purpose, the active ingredient or the active ingredient combination is preferably dissolved or dispersed in an inert liquid and mixed with the carrier, and the solvent is removed during or after the consolidation.

The active ingredient used according to the invention or the active ingredient combination is advantageously prepared by a) providing an active ingredient-containing part of a medicinal plant, where appropriate in comminuted form,
b) adding an aqueous extractant thereto,
c) after the extractant has acted, obtaining a liquid extract phase from the mixture and, where appropriate, repeating the extraction several times, and
d) removing the extractant from the liquid extract phases obtained in this way.

This preferably entails carrying out an extraction with an aqueous extractant at a pH of the mixture in the alkaline range.

The extracted medicinal plant is selected in particular from plants of the genus *Rheum* spp, *Astragalus* spp, *Cassia* spp or *Picea* spp.

In a preferred variant of the preparation process, the total amount of the active ingredient or of the active ingredient combination is mixed in portions with the pharmaceutically acceptable carrier, such as, for example, Avicel or a comparable cellulose-based carrier, in particular microcrystalline cellulose, and the mixing process is repeated after each addition of carrier, but at least one or twice. In particular, a ball mill is used in this case for mixing over a period of from 30 minutes to 3 hours, such as, for example, 1 to 2 hours. It is possible to use for example conventional laboratory ball mills as described in the examples for the mixing. This results in a homogeneous and stable distribution of the active ingredient in the carrier.

In a further variant of the process, the active ingredient core is provided with a gastro-resistant, preferably plasticizer-free, coating.

In a further preferred variant in this connection, the core is sugar-coated.

The invention also relates to liquid dosage forms comprising an active ingredient or an active ingredient combination as defined above in a content of about 0.1 to 20 mg/ml, such as, for example, 0.5 to 15 or 1 to 10 or 2 to 5 mg/ml, in a solvent mixture comprising water and a pharmaceutically acceptable alcohol such as, in particular, ethanol. The solvent mixture is preferably a water/ethanol mixture with an ethanol content of from 10 to 50 or 20 to 40 or 25 to 35% by volume, such as, for example, 30% by volume. These liquid dosage forms are formulated in particular as drops for oral administration.

The invention also relates to semisolid dosage forms comprising an active ingredient or an active ingredient combination as defined above in a content of about 1 to 12, preferably 2 to 6, mg of active ingredient or active ingredient combination (per gram of the formulation) in a conventional semisolid carrier. Suitable gel-forming carriers are generally known and are selected for example from swellable cellulose derivatives such as hydroxypropylmethylcellulose, or polyacrylates such as, for example, carbopol, or gelatin. Dosage forms of this type can be used for example as vaginal gel or vaginal suppositories.

The invention also relates to a composition comprising a solid, semisolid or liquid dosage forms as defined above. Compositions in the sense of the invention are in particular pharmaceutical compositions or medicaments such as, for example, homeopathic remedies, and medicinal plant preparations.

A further aspect of the invention relates to the use of a solid, semisolid or liquid dosage form as defined above or prepared by one of the processes described above or producing a composition as defined above for the treatment of one of the pathological conditions described above. Owing to the excellent tolerability of the active ingredients or active ingredient combinations described above, the invention also relates to the use during long-term therapy, which is possible without limitation in time. The daily dose to be administered in this connection can be in the range from 0.1 to 20 mg or 0.5 to 15 mg, 1 to 10 or 4 to 8 mg of active ingredient or active ingredient combination such as, for example, ERr 731®.

2. Further Specific Refinements of Formulations Used According to the Invention 2.1 Medicaments The invention also includes the production of pharmaceutical compositions (medicaments) for the treatment of an individual, preferably a mammal, in particular a human, productive or domestic animal. Thus, the active ingredients or active ingredient combinations described above are usually administered in the form of pharmaceutical compositions which comprise a pharmaceutically acceptable excipient with at least one active ingredient of the invention, in particular a mixture of a plurality of active ingredients of the invention, and, where appropriate, further active ingredients. These compositions can be administered for example by the oral, local, rectal, transdermal, subcutaneous, intravenous, intramuscular, intraperitoneal, intracutaneous or intranasal route.

Examples of suitable pharmaceutical formulations are solid pharmaceutical forms such as oral powders, dusting powders, granules, tablets, such as coated tablets, gastro-resistant coated tablets, dry-coated, inlay and layered tablets, pastilles, chewable tablets, suckable tablets, sachets, cachets, sugar-coated tablets, capsules such as hard and soft gelatin capsules, pessaries, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops, nose drops, nasal spray and tinctures. It is also possible to use implanted delivery devices for administering inhibitors of the invention. Liposomes, microspheres or polymer matrices can also be used in addition.

In the production of the compositions, active ingredients or active ingredient combinations of the invention are usually mixed with an excipient or diluted. Excipients may be solid, semisolid or liquid materials which serve as vehicle, carrier, adsorbent or medium for the active ingredient or the active ingredient combinations.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, cellulose derivatives such as, for example, methylcellulose, water, syrups and methylcellulose. The formulations may in addition comprise pharmaceutically acceptable carriers or usual ancillary substances such as lubricants, for example tallow, magnesium stearate and mineral oil; wetting agents; emulsifying and suspending agents; preservatives such as methyl and propyl hydroxybenzoates; antioxidants; antiirritants; insulating agents; tablet-coating aids; emulsion stabilizers; film formers; gel fomers; odor-masking agents; taste correctives; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients such as binders, fillers, lubricants, disintegrants or coatings; propellants; dessicants; opacifiers; thickeners; waxes; plasticizers; white oils.

An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996; cf. also Hager's Handbuch der Pharmazeutischen Praxis, Springer Verlag, Heïdelberg.

Solvents which are suitable according to the invention for producing formulations and which should be particularly mentioned are monohydric or polyhydric alcohols such as, in particular, ethanol, glycerol and mixtures thereof with water, such as, for example 1 to 50% by volume ethanol in water.

Dosage forms or pharmaceutical compositions of the invention are produced by using generally known methods of pharmaceutical technology as described for example in Voigt, Pharmazeutische Technologie, 7th edition 1993, Ullstein Mosby, Berlin.

In a preferred embodiment, a pharmaceutical composition which comprises a solid dosage form is provided. This solid dosage form in turn includes an active ingredient-containing solid core with a pharmaceutically acceptable carrier and an active ingredient content of about 1 to 20% by weight, based on the total weight of the core, where the hydroxystilbene-containing active ingredient or the hydroxystilbene-containing active ingredient combination includes a compound selected from resveratrol and piceatannol prodrugs, such as rhaponticin, deoxyrhaponticin, rhapontigenin, deoxyrhapontigenin and astringin; and resveratrol and piceatannol; and the stereoisomeric forms thereof, in each case in the form of their salts or in the phenol form, or combinations of these compounds. Preferred active ingredient combinations are as defined above.

This solid dosage form has for example a total active ingredient content of about 1 to 20 mg, such as, for example, 2 to 10 mg, per dose unit and can be in the form of a pill, a tablet, an extrudate or granules, and for example be sugar-coated. If desired, it may also have a gastro-resistant coating.

The solid dosage form is produced for example by mixing the active ingredient or the active ingredient combination with the pharmaceutically acceptable carrier, and consolidating the mixture to give the active ingredient core. This entails dissolving or dispersing the active ingredient or the active ingredient combination in an inert liquid, mixing it with the carrier and removing the solvent during or after the consolidation. The active ingredient core can then be provided where appropriate with a gastro-resistant coating before the core is sugar-coated in a conventional way.

Liquid dosage forms of the invention are produced for example by dissolving the active ingredient(s) such as, for example, an ERr731® dry extract in a suitable solvent such as, for example, a water/alcohol mixture, where appropriate together with further conventional additions. Active ingredient contents of from 0.1 to 20 or 1 to 10 mg/ml are usually adjusted in this case.

Semisolid dosage forms of the invention, such as, for example, gels, are produced for example by dissolving the active ingredient(s), such as, for example, an ERr 731® dry extract, in a suitable solvent such as, for example, a water/alcohol mixture, alcohol or glycerol, and incorporating the solution into the previously swollen gel former, where appropriate together with further conventional additions. Active ingredient contents of from 1 to 12 or 2 to 6 mg per gram of the formulation are usually adjusted in this case.

The mode and duration of administration of the medicaments of the invention are subject to the decision of the treating physician. The latter can establish a suitable dose and an appropriate dosage regimen depending on the chosen route of administration, on the efficacy of the specific active ingredient composition, the nature and severity of the disorder to be treated, the patient's condition and his response to the therapy. For example, a suitable single dose may comprise about 0.1 to 50 mg, such as, for example, 2 to 12 mg, of active ingredient or active ingredient combination as defined above, and be administered 1 to 3 times a day until the desired result of the treatment is to be observed.

2.2 Dietary Supplements and Food Products

The compositions of the invention also include in particular dietary supplements and food products, especially functional or dietetic food products. The food products of the invention have besides the function mainly related to nutritional value in addition a function related to active ingredients relating in particular to the active ingredient combination of the invention. They are therefore referred to as functional or dietetic food products or foodstuffs. Dietary supplements serve to supplement the daily diet with the active ingredient combination of the invention, in which case the function related to nutritional value of the dietary supplement becomes of less intrinsic importance.

The formulation base for dietary supplements and food products of the invention likewise includes physiologically acceptable ancillary substances in the widest sense, such as, for example, the abovementioned excipients. Ancillary substances in the sense according to the invention may also have a nutritional value and therefore generally be used as dietary component. Nutrients, especially essential nutrients, may also belong thereto.

Nutritional components ordinarily comprise one or more amino acids, carbohydrates or fats and are suitable for human and/or animal nutrition. They include single components, frequently vegetable, but also animal, products, especially sugars, where appropriate in the form of syrups, fruit preparations such as fruit juices, nectar, fruit pulps, purees or dried fruits, for example apple juice, grapefruit juice, orange juice, apple puree, tomato sauce, tomato juice, tomato puree, cereals products such as wheat flour, rye flour, oat flour, cornflour, barley flour, spelt flour, corn syrup, and starches from said cereals; dairy products such as milk protein, whey, yoghurt, lecithin and lactose.

Examples of essential nutrients are in particular vitamins, provitamins, minerals, trace elements, amino acids and fatty acids. Essential amino acids which may be mentioned are isoleucine, leucine, lysine, methionine, phenylalanine, threonine, tryptophan and valine. These also include semiessential amino acids which must be supplied for example during growth phases or deficiency states, such as arginine, histidine, cysteine and tyrosine. Trace elements which may be mentioned are: essential trace elements and minerals such as: iron, copper, zinc, chromium, selenium, calcium, magnesium, sodium, potassium, manganese, cobalt, molybdenum, iodine, silicon, fluorine, chlorine, phosphorus, tin, nickel, vanadium, arsenic, lithium, lead, boron. Fatty acids which may be mentioned as essential for humans are: linoleic acid and linolenic acid, ARA (arachidonic acid) and DHA (docosahexaenoic acid) for infants and possibly EPA (eicosapentaenoic acid) and DHA also for adults. A comprehensive list of vitamins is to be found in "Referenzwerte für die Nährstoffzufuhr", 1st Edition, Umschau Braus Verlag, Frankfurt am Main, 2000, edited by the Deutsche Gesellschaft für Ernährung.

Examples of suitable formulations for dietary supplementation are capsules, tablets, pills, powder sachets, liquid ampoules and bottles with dropper inserts, and the pharmaceutical forms mentioned above.

Food product formulations ordinarily have the usual form and are made available for example as breakfast preparations, in the form of mueslis or bars, sports drinks, complete meals, dietetic preparations such as diet drinks, diet meals and diet bars.

Dietary supplements and food products of the invention are produced by methods familiar to the skilled worker and requiring no further explanation (cf. for example, Hans-Dieter Belitz et al. Lehrbuch der Lebensmittelchemie. Springer-Lehrbuch 5th revised edition 2001. XLIV, 1059 Verlag: SPRINGER, BERLIN)

The content of active ingredients/active ingredient combinations of the invention in the above dietary supplements and food products can vary over a wide range and is for example in a range from 0.01 to 10% by weight, such as, for example, 0.1 to 1% by weight.

2.3 Preparation of a Drug Extract which can be Used According to the Invention

Drug extracts which can be used according to the invention are preferably prepared by
a) providing a hydroxystilbene-containing part of a medicinal plant, where appropriate in comminuted form,
b) adding an aqueous, organic or aqueous-organic extractant thereto,
c) after the extractant has acted, obtaining a liquid extract phase from the mixture, and where appropriate repeating the extraction several times, and
d) removing the extractant from the liquid extract phases obtained in this way.

In particular, the extract obtained in this way includes at least one compound selected from rhaponticin, deoxyrhaponticin, rhapontigenin, deoxyrhapontigenin as salt or in phenolic form, in a stereoilsomeric form thereof, such as cis or trans form, or as mixture of such stereoisomeric forms.

However, the extracted hydroxystilbenes are preferably substantially in the trans form. Salts are in particular the alkali metal and alkaline earth metal phenolates of the above compounds which have one or more free phenolic hydroxyl groups. If a plurality of hydroxyl groups is present, they may be partly or completely in the salt form.

The resulting plant extracts or individual components thereof can, as already mentioned, also be subjected to derivatization reactions in order to obtain so-called functional derivatives.

An active ingredient combination of at least two of the abovementioned compounds is preferably obtained, such as, for example, 2, 3, 4, 5, 6, 7 or 8 individual compounds, with the group of resveratrol precursors (especially deoxyrhaponticin and deoxyrhapontigenin) and of piceatannol precursors (especially rhaponticin and rhapontigenin) each being represented by one compound.

A further preferred embodiment of the process of the invention provides an extract which has a high content of glycosides, in particular glycosides of the type described above, such as, for example, a content of from 30 to 100% by weight, 50 to 100% by weight, 60 to 99% by weight or 80 to 98% by weight or 85 to 96% by weight, in each case based on the total weight of the resulting dry extract. A "dry extract" in the sense of the invention is present in particular when the residual moisture content of water and/or organic liquid (such as extractant) is less than about 5% by weight, in particular less than 2% by weight, such as, for example, 0 to 1.5% by weight or 0.1 to 0.5% by weight, in each case based on the total weight of the resulting dry extract.

A further preferred embodiment provides an extract which is substantially free of aglycone derivatives of rhaponticin and deoxyrhaponticin, such as, in particular, resveratrol and piceatannol. "Substantially free" means an aglycone content of less than 5% by weight, in particular less than 2% by weight such as, for example, less than 1% by weight or 0.1% by weight, such as 0 to 0.05% by weight, in each case based on the total weight of rhaponticin and deoxyrhaponticin.

Active ingredient combinations which are further preferably prepared are those having a total hydroxystilbene content of more than 90% by weight such as, for example, 91 to 100% by weight, or 92 to 99 or 93 to 98 or 94 to 97% by weight.

Further active ingredient combinations which are preferably prepared are those having a content of less than 0.5% by weight, such as, for example, 0-0.49% by weight or 0.001 to 0.3 or 0.01 to 0.2 or 0.01 to 0.1% by weight, of anthraquinone and/or anthraquinoids (in each case based on the dry weight of the active ingredient combination). Anthraquinoids are in this case to be understood in the widest sense as substances having a basic anthraquinone structure.

In a preferred embodiment, the medicinal plant to be extracted is selected from natural plants and plants modified by breeding or recombinant, genetically modified plants which have a content of at least one of the desired ingredients which is higher by comparison with the corresponding unmodified plant. These plants are selected in particular from plants of the genus *Rheum* spp., *Astragalus* spp., *Cassia* spp. or *Picea* spp. or active ingredient-containing plant parts. Non-limiting examples of suitable species of these genera are *Rheum undulatum, Rheum palmatum, Rheum tataricum, Rheum officinale, Rheum wittrockii, Rheum altaicum, Rheum reticulatum, Astragalus complanatus, Cassia garrettiana* and *Picea sitchensis*. It is additionally preferred to employ medicinal plants as single varieties.

The skilled worker is additionally aware that genera/species differing in provenance and differing in age (i.e. harvest at various times of the vegetation period) can be employed, in turn possibly influencing the nature, amount and composition of the hydroxystilbenes and mixtures which can be isolated therefrom. It is likewise possible in principle to use various plant parts such as roots, rhizomes, leaves and/or stalks.

The respective plant part or mixture of plant parts can, if expedient, be mechanically treated such as, for example, ground, chopped, reeled, crushed or cut. If expedient, predrying is also possible, such as, for example, 2 hours to 2 days at 30 to 50° C., in order to reduce the liquid content.

The hydroxystilbene-containing part of the medicinal plant used for the extraction is in particular the root of the medicinal plant, such as, for example, of *Rheum rhaponticum*.

The invention relates in particular to a process in which a hydroxystilbene-containing percolate is prepared from the drug. A "percolation" means a continuous extraction of soluble substances from a drug by continual renewal of the solvent. This results in a permanent concentration gradient, so that a large part of all the soluble substances goes into the extract.

An alternative possibility is also a continuous or periodic mixing of the batch such as, for example, by stirring or shaking.

The temperature during the extraction according to the invention is usually in the range from 10 to 50° C., such as, for example, 25 to 35° C. The pressure is usually atmospheric pressure. If a speeding up of the rate of extraction or quality of the extract can be achieved, the pressure may also be varied during the extraction, such as, for example, raised or lowered.

The extraction may take, depending on the chosen conditions such as the nature of the drug, batch size, extractant and temperature used, from 1 hour to several days, such as, for example, 10 to 72 hours.

The extraction process can if necessary be repeated several times in order to ensure that isolation in particular of the desired ingredients is as complete as possible. The ratio by weight of introduced drug to liquid extractant may vary over a wide range and from extraction step to extraction step. The ratio by weight of drug to extractant is typically in the range from 10:1 to about 1:200 or about 1:2 to 1:50, or 1:4 to 1:10.

In one variant of the process, an extraction is carried out with an aqueous extractant which is substantially free of organic solvent, such as, in particular, water, preferably purified water, at a pH of the mixture in the alkaline range, with the pH of the mixture being in particular in the range from about 11 to 12, such as, for example, about 11.3 to 11.8.

The pH of the mixture is adjusted for example with the aid of an inorganic base selected from alkali metal and alkaline earth metal hydroxides such as, for example, calcium hydroxide or calcium oxide. It is possible for this purpose for example to prepare a concentrated quicklime solution by dissolving 3 to 8 parts of CaO in 20 parts of purified water. This solution is strongly alkaline and has a pH in the range from about 12 to 13, such as, for example, of about 12.4 to 12.6.

The ratio of the amounts of introduced drug to base such as, for example, calcium hydroxide (calculated as calcium oxide) can be according to the invention in the range from about 5:1 to 20:1, such as about 8:1 to 12:1 or 9:1 to 11:1.

The process is preferably carried out in such a way that the desired hydroxystilbenes are precipitated from the resulting alkaline liquid extract phase, for example by adjusting the pH of the extract to a value in the range from about 3 to 4, such as, for example, 3.2 to 3.8, or 3.4-3.6, and, where appropriate, subsequently removing the precipitate, washing where appropriate and drying where appropriate.

Used for the acidification is any inorganic or organic acid, such as, for example, hydrochloric acid or sulfuric acid, but in particular organic acids such as formic acid or acetic acid.

Before removal of the precipitate it may be expedient to leave the batch to stir for some hours or days in order to achieve precipitation which is as quantitative as possible of the desired extracted ingredients.

The precipitate can be washed for example with purified water, and this serves in particular to remove remaining acid.

Remaining liquid is removed from the extract by drying, e.g. at 30 to 50° C. or 35 to 45° C., for example over a period of from 1 to 100 hours, until the residual moisture is in the range indicated above. The drying takes place in a manner known per se, e.g. in a drying oven. Freeze drying is likewise possible.

The invention is now further explained by means of the following nonlimiting examples and with reference to the appended figures.

EXPERIMENTAL SECTION

General Methods

Determination of Stilbenes by High-Pressure Liquid Chromatography (HPLC) in the Dry Extract from Rhapontic Rhubarb Root
a) Sample Preparation:
50 mg of extract, mixed with 40 ml of a mixture of acetone and water (1:1) in an amber glass vessel, treated in an ultrasonic bath for 15 minutes and made up to 50 ml with the solvent mixture and then diluted 1:10 with the solvent mixture.
b) Procedure for the Chromatography:
A high-pressure liquid chromatography (HPLC) is carried out on a portion of the solution obtained above, with the following system parameters:

| | |
|---|---|
| Sample loop: | 20 µl |
| Column: | Lichrospher 5µ RP 18, 250 × 4 mm |
| Precolumn: | Lichrospher 5µ RP 18, 5 × 4 mm |
| Column temperature: | 25° C. |
| Eluent A: | Acetonitrile/dist. water/phosphoric acid 85%, 15/85/0.05 (parts by volume) |
| Eluent B: | Acetonitrile/dist. water/phosphoric acid 85%, 80/20/0.05 (parts by volume) |
| Flow rate: | 1.5 ml/min |
| Column flushing: | 15 min with eluent 50% B; equilibration time 15 min |
| Detection: | 310 nm |
| HPLC: | Kontron Kroma 2000 |
| Gradient: | Time    % B |
| | 0.0       0 |
| | 0.5       0 |
| | 7.5      75 |
| | 8.5     100 |
| | 9.5       0 |
| | 12.5      0 |

The retention times resulting under the system conditions indicated above are as follows:

| | |
|---|---|
| Rhaponticin: | about 5.5 min |
| Deoxyrhaponticin: | about 6.8 min |
| Rhapontigenin: | about 7.2 min |
| Deoxyrhapontigenin: | about 9.0 min |

For a quantitative determination, the respective peak areas are found and compared with the corresponding peak areas of a standard extract of known composition.

Preparation Example 1

Preparation of the Dry Extract ERr 731 from Rhapontic Rhubarb Root with an Aqueous Calcium Hydroxide Solution A dry extract is prepared from rhapontic rhubarb root employing the following:

| | |
|---|---|
| Drug (radix rheum rhaponticum) | 50.0 kg |
| Calcium oxide | 5.0 kg |
| Purified water | 190.0 kg |

Acetic acid (as necessary to adjust the required pH)

The yield which can be achieved in this case is between 2 and 3 kg per 50 kg of drug.

The preparation takes place in the following steps:
a) Firstly 5 kg of calcium oxide are introduced into a plastic tub and made into a slurry with 20 kg of purified water. The formation of calcium hydroxide (quicklime) which takes place under these conditions leads to a large rise in temperature of the solution. The calcium hydroxide can therefore be used further only after cooling. The temperature of the solution is then 30° C. to 35° C.
b) 50 kg of drug are introduced into a mixer, and the above-mentioned quicklime is added. In order to remove the quicklime as completely as possible from the plastic tub, it is rinsed with 10 kg of purified water. This washing liquid is likewise put in the mixer.
c) The drug homogeneously mixed with quicklime is introduced into a percolator and covered with 160 kg of purified water. The percolator remains closed for 48 hours. The percolate is then collected in a suitable vessel at a flow rate of 50 ml/min. The percolation is continued until no further percolate emerges. The drug mass is not squeezed out after completion, but is discarded.

d) While monitoring continuously, concentrated acetic acid is added to the percolate until a pH in the range from 3.4 to 3.6 is reached. In order to achieve precipitation of the extract which is as complete as possible, the mixture is left to stand for 5 days.

e) The dry extract is obtained by filtration through Büchner funnels under applied vacuum. Finally, the extract is washed with 10 to 20 kg of purified water.

f) The dry extract obtained after filtration is dried in a drying oven at 40° C. until a residual moisture tolerance not exceeding 1% is reached.

Rhaponticin is readily soluble in aqueous solutions with an alkaline pH range, whereas it is precipitated as yellowish substance in the acidic pH range (pH 3.4-3.6). Use is made of this for its isolation. Since, besides other organic acids, the root in particular has a high content of oxalic acid (⅔ in water-soluble and ⅓ in bound form), this must be neutralized during the isolation in order to prevent the pH drifting into the acidic range and thus to inhibit premature precipitation of the rhaponticin. This is achieved by using calcium oxide. The latter is employed as quicklime solution with a pH of 12.4-12.6.

Homogeneous mixing of the quicklime with the drug alters the pH of the mixture. It is then in the range from 11.3 to 11.8, thus preventing precipitation of rhaponticin, because the phenolic form has been converted into a phenolate form. Despite the high oxalic acid content, the pH can be kept in the alkaline range. This is attributable to the fact that the calcium hydroxide reacts with oxalic acid and forms insoluble and nontoxic calcium oxalate.

Rhaponticin is extracted from the root by the subsequent percolation with purified water. After completion of the percolation, a pH of 3.4 to 3.6 is adjusted by adding acetic acid. This pH shift from the alkaline to the acidic range leads to a precipitation of rhaponticin through conversion back into the phenolic form. In order to achieve precipitation of rhaponticin which is as complete as possible, the mixture is left to stand for 5 days. It is then filtered. Rhaponticin remains as yellowish substance on the filter.

The above statements about rhaponticin apply correspondingly to the other hydroxystilbene active ingredients isolated according to the invention.

Preparation Example 2

Preparation of a Dry Extract from Rhapontic Rhubarb Root with Various Organic Solvents The constituents mainly detectable in the rhapontic rhubarb root used as drug here belong to the group of hydroxystilbenes. Present from this group in the roots are rhaponticin (Rh) with a content of about 6% and deoxyrhaponticin (DRh) with a content of about 4%.

It is possible by exposure to the solvent systems indicated below, in a 100-fold quantity at room temperature for 10 minutes with shaking or stirring, to extract the proportions summarized below:

| Ethanol 86% | Rh | 100.8% |
| | DRh | 99.5% |

-continued

| Ethanol 15% | Rh | 77.1% |
| | DRh | 75.5% |
| Acetone | Rh | 88.3% |
| | DRh | 96.6% |
| Water, alkaline (pH 11, adjusted with CaO solution) | Rh | 75.5% |
| | DRh | 60.5% |

No useful results were achieved with heptane.

The respective yields of crude extracts in proportions by mass (based on drug employed) are as follows:

| Ethanol 86% | 35.5% |
| Ethanol 15% | 32.2% |
| Acetone | 21.4% |
| Heptane | 0% |
| Water, alkaline | 4.5% |

Extraction of rhapontic rhubarb root with ethanol-water mixtures leads to an extract which, besides the main constituents rhaponticin (about 30%) and deoxyrhaponticin (about 22%), comprises a further stilbene, which has not as yet been investigated, in a proportion of about 20% in the extract. Besides these, the aglycones rhapontigenin (about 8%) and deoxyrhapontigenin (about 2%) and a further 9 compounds which total about 20% are obtained.

The results on extraction with acetone are fundamentally the same.

Extraction with alkaline water (cf. conditions in preparation example 1) leads to an extract of greater purity.

The main constituents rhaponticin and deoxyrhaponticin are present in a proportion of about 97% in the dry extract. Rhapontigenin and deoxyrhapontigenin together amount to a proportion of 1.1% of the extract, whereas the stilbene which has not yet been investigated is present in a proportion of only 0.2%. A further 3 compounds are present in a proportion of 2.5%.

Formulation Example 1

Production of a Solid Dosage Form—Minitablet

1. Production of the Tablet Core:

A solid tablet core is produced using the following active ingredients and ancillary substances in the stated ratios of amounts (P=parts by weight). The ingredients are mixed and tabletted in three different ways:

a) Tablet Core Formulation:

| Purified dry extract according to preparation example 1 from rhapontic rhubarb root (ERr 731 ®) | 3.6 P |
| Microcrystalline cellulose (e.g. Avicel ®) | 57.0 P (±40%) |
| Sorbitol | 8.0 P (±40%) |
| Talc | 2.5 P (±40%) |
| Makrogol 6000 (polyglycol) | 1.6 P (±40%) |
| Polyvidone (K value about 25, e.g. Kollidon ® 25) | 1.6 P (±40%) |
| Sodium dodecyl sulfate (e.g. Texapon ® K 12) | 0.5 P (±40%) |
| Magnesium stearate (vegetable) | 0.8 P (±40%) |
| | 75.6 P (±40%) |

It is possible by varying the weighed amount of ERr 731® and/or varying the amount of microcrystalline cellulose to obtain any desired ERr 731® contents in the untreated core (such as, for example, 2, 4, 6, 8, 10, 12 mg per tablet).

b) Mixing of Drug and Carrier

Mixing variant a:

1.2 P of ERr® 731 are triturated in portions with Avicel® in a ball mill and then, after addition of the other ancillary substances, mixed and tabletted as described below.

Mixing variant b:

ERr 731 (1 g/l of solvent) is dissolved in a suitable solvent (e.g. ethanol/water mixture 86% v/v ethanol) and adsorbed on Avicel®, dried (at 40° C. for at least 48 hours) and, after addition of the other ancillary substances, mixed and tabletted as described below.

Mixing variant c:

The total amount of Avicel® is divided into three equal portions. The first portion is mixed with the total amount of ERr731® and triturated in a laboratory ball mill (e.g. type 1-25 LK, Alpine, Augsburg) for at least 120 minutes. The second portion of Avicel® is then added, and the mixture is again triturated in the laboratory ball mill for at least 120 minutes. After addition of the third portion of Avicel®, brief mixing is again carried out. Subsequently, after addition of the other ancillary substances, mixing and tabletting are carried out as described below.

It is surprisingly possible with this mixing variant to reduce markedly the tendency to inhomogeneity and, even with small dose units, to adjust an extremely uniform active ingredient content of not more than ±5% by weight (determined according to Ph. Eur. 5th edition 2005 (5.0/2.09.06.00)).

c) Tabletting:

The mixture of Avicel® and active ingredient is sieved through a sieving machine (sieve diameter 1.2 mm) into a suitable mixing container and, after addition of the stated tabletting aids (without magnesium stearate), mixed in a suitable mixer (e.g. drum hoop mixer of type Standard RR M 200, from Engelsmann AG/Ludwigshafen) for at least 30 min. Addition of magnesium stearate is followed by mixing again for at least 5 min.

The compression takes place in a suitable tablet press (e.g. rotary of type Perfecta Fette 2000, from Fette/Schwarzenbeck):

Core weight: 84 mg±4.2 mg maximum variation

Punch: 7 mm diameter, domed

The ERr-731 content per core is about 4 mg±5%.

2. Production of the Gastro-Resistant Coated Tablet

After removal of dust from the tablet cores with Eudragit, a gastro-resistant coating of cellulose acetate phthalate and diethyl phthalate, dissolved in isopropanol and ethyl acetate, is applied to the tablet cores using a coating system.

Macrogol is dissolved in purified water. The ingredients sugar (sucrose or isomalt), calcium carbonate, talc, titanium dioxide and the two povidones are mixed and stirred into the liquid. The suspension is stirred in a jet flow mixer (e.g. Rototron of type RTA 70-50) for 20 minutes.

The sugar-coating suspension is applied to the sealed core with the aid of an automatic coater. The process is repeated until an average weight of 150 mg per coated core is reached. Finally, the polishing wax is applied and then rolling is continued until a high gloss is obtained.

Final weight of the gastro-resistant coated tablet:

150 mg±7.5 mg maximum variation.

In this way, two different tablet forms—one containing sugar and one sugar-free—are produced, employing the respective ancillary substances in the parts by weight indicated below.

a) Gastro-Resistant Coated Minitablet—Containing Sugar—with Plasticizer in the Coating

| Ancillary substances: | | |
|---|---|---|
| Coating: | Eudragit L12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |
| | Talc | 2.000 kg (±40%) |
| Sugar coating: | Talc | 7.182 kg (±40%) |
| | Sugar | 28.747 kg (±40%) |
| | Calcium carbonate | 6.410 kg (±40%) |
| | Titanium dioxide E 171 | 0.635 kg (±40%) |
| | Povidone | 0.756 kg (±40%) |
| | (K value about 25, e.g. Kollidon ® 25) | |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) | b) Gastro-Resistant Coated Minitablet—Sugar-Free—with Plasticizer in the Coating

| Ancillary substances: | | |
|---|---|---|
| Coating: | Eudragit L12.5% dry matter | 1.350 kg (±40%) |
| | Diethyl phthalate | 1.749 kg (±40%) |
| | Cellulose acetate phthalate | 7.770 kg (±40%) |
| | Isopropyl alcohol | 75.600 kg (±40%) |
| | Ethyl acetate | 77.600 kg (±40%) |
| Sugar coating: | Talc | 7.482 kg (±40%) |
| | Sorbitol and/or isomalt | 28.747 kg (±40%) |
| | Calcium carbonate | 6.410 kg (±40%) |
| | Titanium dioxide E 171 | 0.635 kg (±40%) |
| | Povidone | 0.756 kg (±40%) |
| | (K value about 25, e.g. Kollidon ® 25) | |
| | Povidone (K value about 90) | 0.332 kg (±40%) |
| | Macrogol 35,000 | 0.635 kg (±40%) |
| | Water | 10.500 kg (±40%) |
| Polish: | 95% carnauba wax, 5% bleached wax (e.g. Capol 1295 PH) | 0.108 kg (±40%) |

Formulation Example 2

Production of a Solid Dosage Form—Minitablet Containing Sugar without Plasticizer 1. Production of the Tablet Core Production takes place in analogy to formulation example 1.

2. Production of the Gastro-Resistant Coated Tablet

Production takes place in analogy to formulation example 1, but with use of shellac (variant A) or Aqoat (variant B) instead of cellulose acetate phthalate/diethyl phthalate (plasticizer).

| Ancillary substances: | | kg (±40%) |
|---|---|---|
| a) Variant A | | |
| Coating: | Eudragit L12.5% dry matter | 0.400 |
| | CAPOL 5270 PH 8% (shellac solution) = | 60.000 |

| Ancillary substances: | | kg (±40%) |
|---|---|---|
| | 4.8 kg dry matter (shellac) | |
| | Isopropyl alcohol | 4.000 |
| | Ethanol 96% | 3.200 |
| | Talc | ..2.000 |
| Sugar coating: | Talc | 7.182 |
| | Sugar | 28.747 |
| | Calcium carbonate | 6.410 |
| | Titanium dioxide E 171 | 0.635 |
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |
| | b) Variant B | |
| Coating: | Eudragit L12.5% dry matter | 0.400 |
| | Aqoat | 5.420 |
| | Hydroxypropylmethylcellulose acetate succinate | |
| | Distilled water | 12.500 |
| | Isopropyl alcohol | 4.000 |
| | Ethanol 86% | 55.000 |
| Sugar coating: | Talc | 9.182 |
| | Sugar | 28.747 |
| | Calcium carbonate | 6.410 |
| | Titanium oxide E 171 | 0.635 |
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

Formulation Example 3

Production of a Solid Dosage Form—Minitablet Sugar-Free without Plasticizer

1. Production of the Tablet Core
Production takes place in analogy to formulation example 1, but using isomalt instead of Avicel.
2. Production of the Gastro-Resistant Coated Tablet
Production takes place in analogy to formulation example 2, but using isomalt instead of sugar.

| Ancillary substances: | | kg (±40%) |
|---|---|---|
| | a) Variant A | |
| Coating: | Eudragit L12.5% dry matter | 0.400 |
| | CAPOL 5270 PH 8% | 60.000 |
| | (shellac solution) = | |
| | 4.8 kg dry matter (shellac) | |
| | Isopropyl alcohol | 4.000 |
| | Ethanol 96% | 3.200 |
| | Talc | 2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |
| | b) Variant B | |
| Coating: | Eudragit L12.5% dry matter | 0.400 |
| | Aqoat | 5.420 |
| | Distilled water | 12.500 |
| | Isopropyl alcohol | 4.000 |
| | Ethanol 86% | 55.000 |
| | Talc | ..2.000 |
| Sugar coating: | Talc | 7.182 |
| | Isomalt | 28.747 |
| | Calcium carbonate | 6.410 |
| | Titanium oxide E 171 | 0.635 |
| | Polyvidone | 0.756 |
| | (K value about 25, e.g. | |
| | Kollidon ® 25) | |
| | Povidone (K value: about 90) | 0.332 |
| | Macrogol 35,000 | 0.635 |
| | Water | 10.500 |
| Polish: | 95% carnauba wax | 0.108 |
| | 5% bleached wax | |
| | (e.g. Capol 1295 PH) | |

Formulation Example 4

Production of a Semisolid Dosage Form—Vaginal Gel

Production takes place using conventional methods by the two following variants:

a) Variant A:

Hydroxypropylmethylcellulose (hypromellose USP) or another gel former is allowed to swell with 2-10% by weight in purified water. The ERr 731® (preparation example 1), dissolved in glycerol, is then incorporated. The amount of glycerol may be up to 50% of the weight of the gel. ERr 731® can be dissolved up to 0.5% by weight in glycerol. If necessary, preservatives (e.g. sorbic acid and its salts) can be added to the gel. Adjustment of the pH is also possible. As alternative to glycerol it is also possible to use 30-86% by volume ethanol.

b) Variant B:

Carbomer (Carbopol) is dissolved with 0.5-5% by weight in purified water, and the desired pH is adjusted (e.g. KOH, NaOH, NH$_3$). If necessary, a preservative (e.g. sorbic acid and its salts) is admixed. After formation of a clear gel, ERr 731® (preparation example 1) is dissolved up to 0.5% by weight in 30-86% by volume ethanol and added. As alternative to ethanol, it is also possible to use glycerol.

Formulation Example 5

Production of a Semisolid Dosage Form—Vaginal Suppositories

Suppositories with a size of 1 to 15 g with a content of 1 to 12 mg of ERr 731® (preparation example 1) dissolved in glycerol (85% n 20/D=1.45085) are produced in a conventional way by two different variants.

| a) Variant A: Formulation: | |
| --- | --- |
| Gelatin | 1 part |
| Purified water | 2 parts |
| Glycerol 85% (+ERr 731 ®) | 5 parts | b) Variant B:

Same formulation but with suitable preservatives such as, for example, sorbate, benzoate, PHB ester.

The gelatin is introduced in each case into purified water and allowed to swell until the mixture has become glassy. Glycerol 85% with active ingredient is then added and heated, but not above 65° C. The suppositories are then cast in a conventional way.

Formulation Example 6

Production of a Liquid Dosage Form—Drops

| a) Dissolving tests with ERr 731 ® in ethanol and glycerol: | |
| --- | --- |
| Content of the extract: | |
| 61.9% rhaponticin | |
| 29.9% deoxyrphaponticin | |
| Test A: 200 mg of dry extract in 50 ml of glycerol R: | |
| 55.1% rhaponticin | (89.0% of theory) |
| 27.1% deoxyrhaponticin | (90.6% of theory) |
| Test B: 200 mg of dry extract in 50 ml of ethanol 30% R: | |
| 52.2% rhaponticin | (84.3% of theory) |
| 25.2% deoxyrhaponticin | (84.2% of theory) |
| Test C: 200 mg of dry extract in 50 ml of ethanol 50% R: | |
| 58.8% rhaponticin | (95.0% of theory) |
| 29.0% deoxyrhaponticin | (97.0% of theory) |
| Test D: 200 mg of dry extract in 50 ml of ethanol 86% R: | |
| 59.8% rhaponticin | (96.6% of theory) |
| 29.5% deoxyrhaponticin | (98.7% of theory) | b) Production of Drops:

Drops are produced by dissolving dry extract according to test B in ethanol 30% R and filtering where appropriate. AglyconeeeShellacShellacShellacShellac Test Example 1

Pharmacokinetics and In Vivo Accumulation and Metabolism of the Ingredients of ERr 731® a) Pharmacokinetics of ERr 731® Ingredients in Female Subjects

The intention was to check whether, after oral intake of ERr 731®, one of the ingredients of this active ingredient combination can be found again in the blood, in order to demonstrate that at least one of the constituents of this active ingredient combination or its metabolites is bioavailable.

A volunteer took 10 tablets of ERr 731® (dosage=40 mg of ERr 731®) with liquid in the morning (8.00 h). Subsequently, 10 ml of blood was taken at various times (as indicated in FIG. 1) and the plasma was obtained by centrifugation.

These plasma samples were processed as follows: 500 µl of plasma were mixed with 25 µl of an internal standard working solution (2.5 ng/µl rhaponticin or rhapontigenin in methanol) and then mixed with 500 µl of isotonic NaCl solution and 2.5 ml of diethyl ether/butanol (9/1; v/v). After shaking and centrifugation (10 minutes at 4600 rpm), about 2 ml of the supernatant were removed and dried under a stream of nitrogen (at 60° C.). The pellet was taken up in 50 µl of methanol. Addition of 200 µl of distilled water was followed by renewed mixing, and 200 µl were pipetted into autosampler tubes (light-protected). 30 µl of the samples were injected for analysis into an LC-MS/MS system (PE Sciex API 3000). Chromatographic separation of the analytes took place on a Phenomenex Polymer X column with a gradient of an ammonium buffer solution and an acetonitrile/methanol mixture as mobile phase.

Figure 2A:
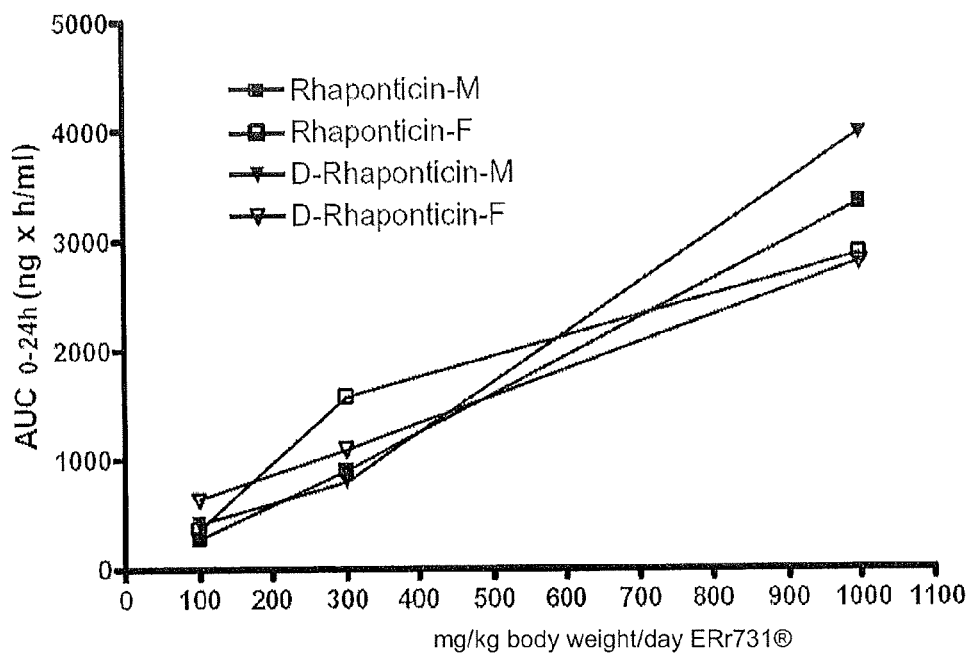
FIG. 2a shows the dose-dependent accumulation (AUC 0-24 h (ng×h/ml)) of rhaponticin and deoxyrhaponticin in dog plasma (M=male, F=female) after administration of ERr 731®; the aglycones rhapontigenin and deoxyrhapontigenin are undetectable.

The analyzed results are summarized in FIG. 1. Rhaponticin was detected in the blood, with a maximum at 3-4 hours (FIG. 1), whereas rhapontigenin could not be found. Since rhaponticin is one of the main ingredients of ERr 731®, it can be assumed that rhaponticin is an activity-codetermining ingredient of ERr 731®. This is all the more surprising since it was previously assumed that only the aglycones, but not the glycosylated hydroxystilbenes, are active (Park et al., Arch Pharm Res. 2002; 25:528-533).

b) Vivo Accumulation and Metabolism of the Ingredients of ERr 731® in Dog Plasma 1) 20 male and 20 female dogs (pure-bred beagles, weight 6-9 kg, age 6-8 months) received 100 (4 animals each), 300 (4 animals each) and 1000 (6 animals each) mg/kg of body weight/day ERr 731®. On day 1, 5 ml of blood were taken from the animals after 0, 0.5, 1, 2, 4, 8 and 24 hours in each case, and plasma was obtained. The analysis as described in section a) was carried out thereon in order to detect rhaponticin, deoxyrhaponticin, rhapontigenin, deoxyrhapontigenin, resveratrol and piceatannol in blood. The results of the test are depicted in FIG. 2a.

Figure 2B:
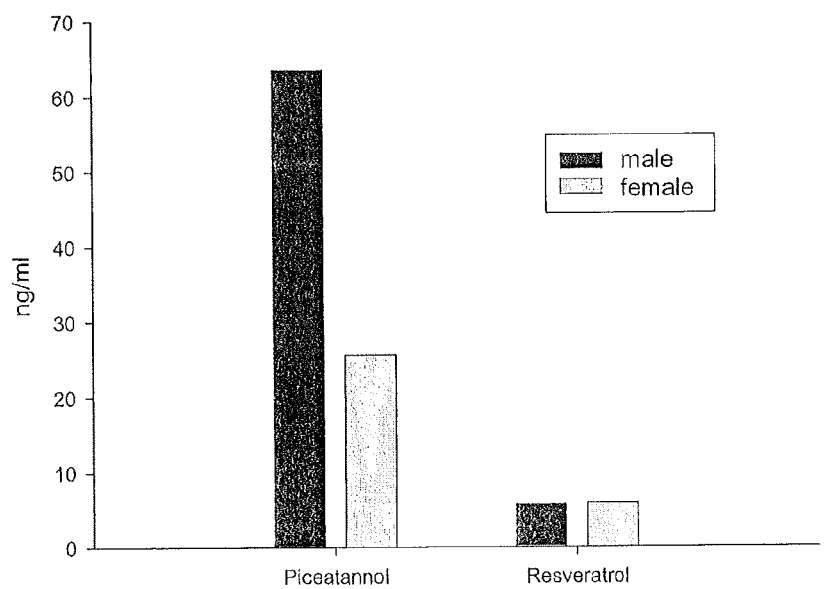
FIG. 2b shows the formation of piceatannol and resveratrol in vivo in male and female dogs 24 hours after administration of 100 mg of ERr 731®/kg of body weight.

2) For further elucidation of the mode of action, ERr 731® was administered orally by capsule to 3 male and 3 female dogs (pure-bred beagles, weight 6-9 kg, age 6-8 months) in a dose of 100 mg of ERr 731®/kg of body weight. After various times, blood was taken from the animals and blood plasma was obtained. The plasma was investigated for ERr 731® ingredients and metabolites. It was surprisingly possible to detect both in male and in female animals significant amounts of the metabolite piceatannol and small amounts of the metabolite resveratrol. Maximum plasma levels of these metabolites were reached after about 24 h. The plasma levels of piceatannol were distinctly higher than those of resveratrol. The results of the test at the 24 h timepoint are depicted in FIG. 2b.

The results of the tests described above surprisingly demonstrate that the main ingredients of ERr 731® are absorbed as glycosides in the body after oral administration and are detectable as such in the bloodstream in a dose-dependent manner, and thus are systemically bioavailable, whereas their direct aglycones rhapontigenin and deoxyrhapontigenin were undetectable. It was additionally possible to show that at high dosage the corresponding metabolites resveratrol and, in particular, piceatannol are also formed in the body.

Test Example 2

Estrogen Receptor β (Erβ) Activation by ERr 731® and its Metabolites in the ERβ-Expressing Endometrial Adenocarcinoma Cell Line HEC-1B HEC-1B cells, a human endometrial adenocarcinoma cell line, do not express either ERα or ERβ. They therefore represent a possible way of investigating, in a human and endometrial context, ligand-dependent effects of substances on the transactivation mechanisms in relation to different receptor subtypes and different estrogen-responsive promoters.

An established ERβ/mC3-luciferase system was employed. For this purpose, HEC-1B cells were applied in 24-well plates with a density of 95 000 cells/well (in Dulbecco's modified Essential Medium (DMEM/F12)). The next day, they were cotransfected with an ERβ-containing construct (hERβ/pSG2) and a triple-ERE-containing promoter/luciferase construct (mC3-Luc/pGL2) (Hillisch et al. Dissecting physiological roles of estrogen receptor alpha and beta with potent selective ligands from structure-based design. Mol. Endocrinol. 2004 July; 18:1599-609). The transient transfection took place using DOTAP (N-[1-(2,3-dioleoyloxy)]-N,N,N-trimethylammoniumpropane methylsulfate, Roth) as described by the manufacturer.

After 24 hours, the cells were treated with appropriate concentrations of the substances or substance mixtures to be investigated. Estradiol (10 nm) served as positive control, and a comparable volume of dimethyl-sulfoxide (DMSO) was employed as solvent control. The incubation time was 24 hours. The cells were then lysed. The Luciferase Assay® kit (Promega) was used to determine the luciferase activity on the one hand, and the BCA® kit (Sigma) was used to determine the protein content on the other hand. The resulting specific luciferase activities of the substances to be investigated were then compared with the DMSO control (100%).

At least three transfection experiments were carried out for each test substance. After calculation of the relative luciferase activity in relation to the negative control (DMSO) for each single experiment (set at 100%), the corresponding averages and standard deviations are formed. The results are represented graphically in the form of a bar diagram. Student's test was used to calculate the significance, the latter being fixed as follows: *$p<0.05$; $p<0.01$; *$p<0.001$.

Figure 3A:
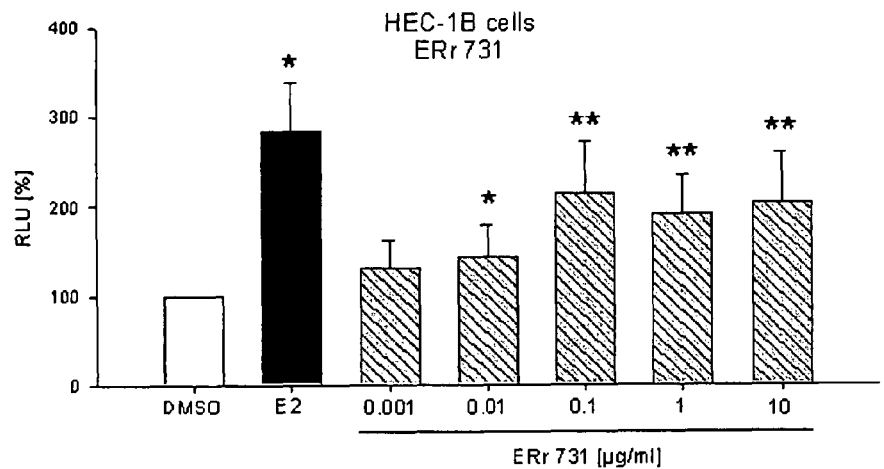
FIG. 3 shows the result of experiments on the activation of the estrogen receptor β (ERβ) by the active ingredient combination ERr 731® in the human endometrial carcinoma cell line HEC-1B (FIG. 3a); the aglycones trans-rhapontigenin (FIG. 3b) and deoxyrhapontigenin (FIG. 3c) are effective only at higher concentrations (E2=estradiol; RLU=relative luciferase units); *=p<0.05; **=p<0.01
Figure 3B:
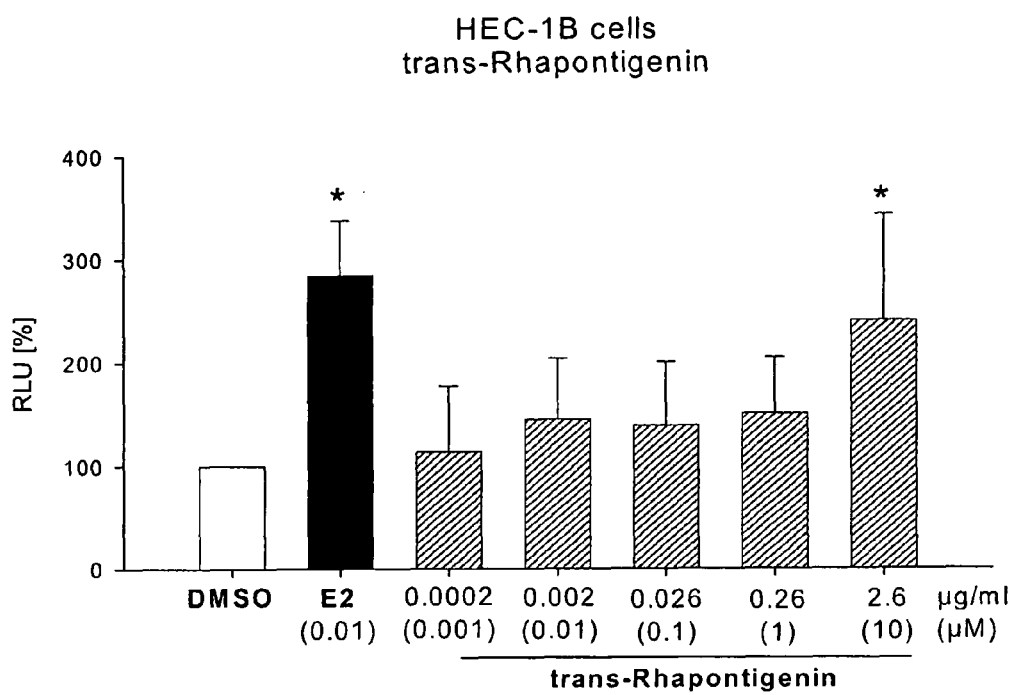
Figure 3C:
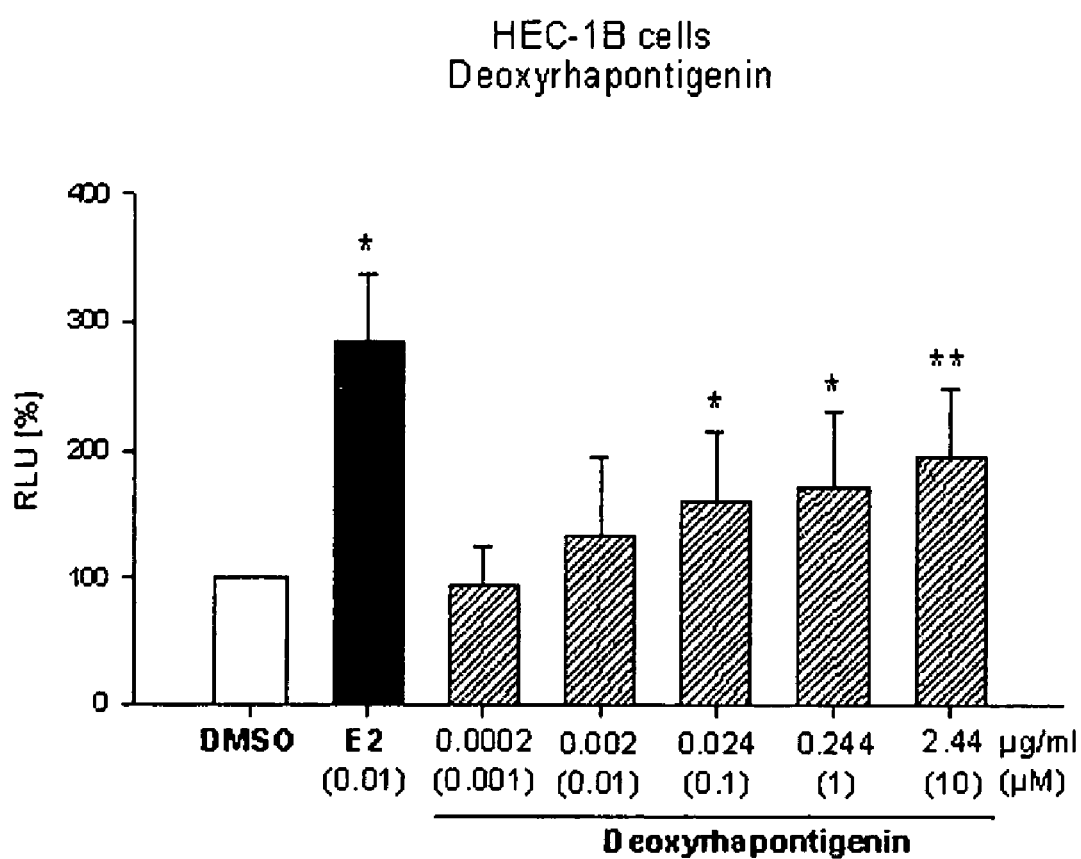

The results for ERr 731® are depicted in FIG. 3a, for trans-rhapontigenin in FIG. 3b and for deoxyrhapontigenin in FIG. 3c. They show that the substances activate the ERβ dose-dependently and thus can be employed according to the invention.

The results of the tests described above demonstrate the surprising finding that, contrary to previous assumptions, the "precursors" of resveratrol and piceatannol, i.e. the glycosides rhaponticin and deoxyrhaponticin (as main constituents of ERr 731®) can be taken up per se by human cells. Skilled workers have previously assumed that these glycones are non-absorbable (cf. Park et al, Arch. Pharm. Res. 2002, 25 (4), 528-533). A further surprising fact is that the active ingredient combination ERr 731® has greater activity than the corresponding aglycones rhapontigenin and deoxyrhapontigenin, which are not detectable under physiological conditions, however (cf. results of above test example 1, FIG. 2a).

It has thus been possible to show for the first time by the present invention the direct pharmacological activity of the glycosides rhaponticin and deoxyrhaponticin (as main constituents of ERr 731®).

Test Example 3

Effect of ERr 731® on IL-6 a) Long-Term Effect in Humans

In vivo investigations on IL-6 levels in the blood took place during a 15-month observation study involving 82 patients with menopausal symptoms. These patients took one tablet of ERr 731® (Phytoestrol® N; dosage=4 mg of ERr 731®) once a day. Blood was taken before intake (IC) and after 3 months in each case, and IL-6 was detected in the serum by means of a specific ELISA (Pharmingen BD, Heidelberg).

Figure 4:
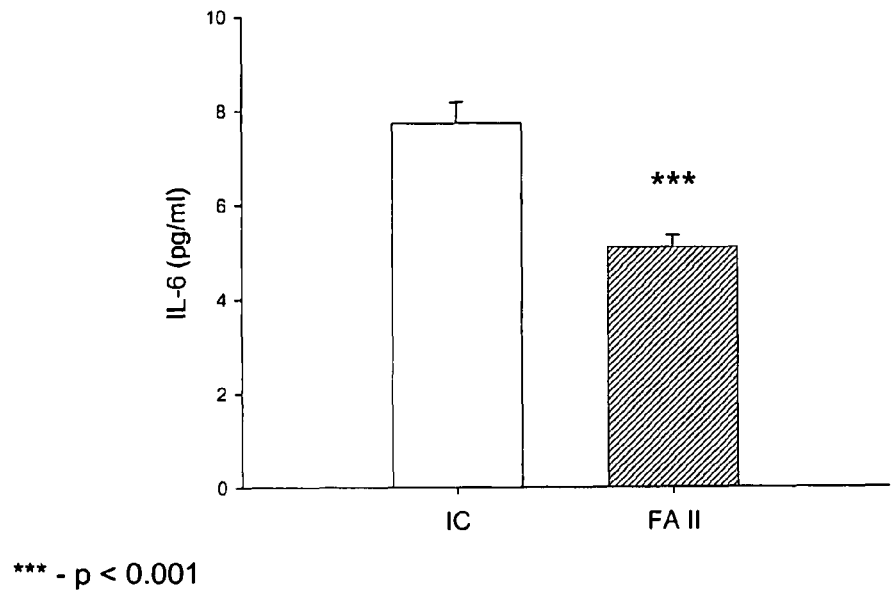
FIG. 4 shows the effect on the IL-6 level of treatment of patients with menopausal symptoms (FA II) with from ERr 731® for 15 months. It was found that the IL-6 levels were significantly reduced with ERr 731® compared with the levels before the first intake (IC); ***=p<0.001.

It was surprisingly found for the first time in these patients, after treatment for 15 months (FA II), that with ERr 731® the IL-6 levels were significantly reduced compared with the levels before the first intake (IC). This surprising finding is depicted in appended FIG. 4.

b) Investigation of the Effects of ERr 731® on the Cytokine-Stimulated Release of IL-6 from Human Tumor Cells The human tumor cell line A549 (lung carcinoma cells) was used for the tests.

These cells represent a model system for IL-6-producing cells in inflammatory disorders (Billich et al., Basal and induced sphingosine kinase 1 activity in A549 carcinoma cells: function in cell survival and IL-1β and TNF-α induced production of inflammatory mediators. Cell Signal 2005; 17: 1203-1217).

A549 cells are human lung carcinoma cells (58-year old male patient, 1972) which have the ability to form tumors in suitable mouse models. These epithelial cells are a widely used cell culture model for the pharmacological influencing of carcinoma cells in the lung.

A549 cells grow adherently, have a generation time of about 30 h and are cultured in FCS-containing (10%) DMEM cell culture medium. Stimulation was carried out with a combination of the following recombinant human cytokines:
IL-1β (50 ng/ml)
TNFα (50 ng/ml).

For the stimulation, confluent A549 cells (in 6-well plates) in DMEM stimulation medium (without phenol red, serum-free, in 0.01% fatty acid-free BSA) were activated with IL-1β/TNFα +/−ERr 731®.

Figure 5:
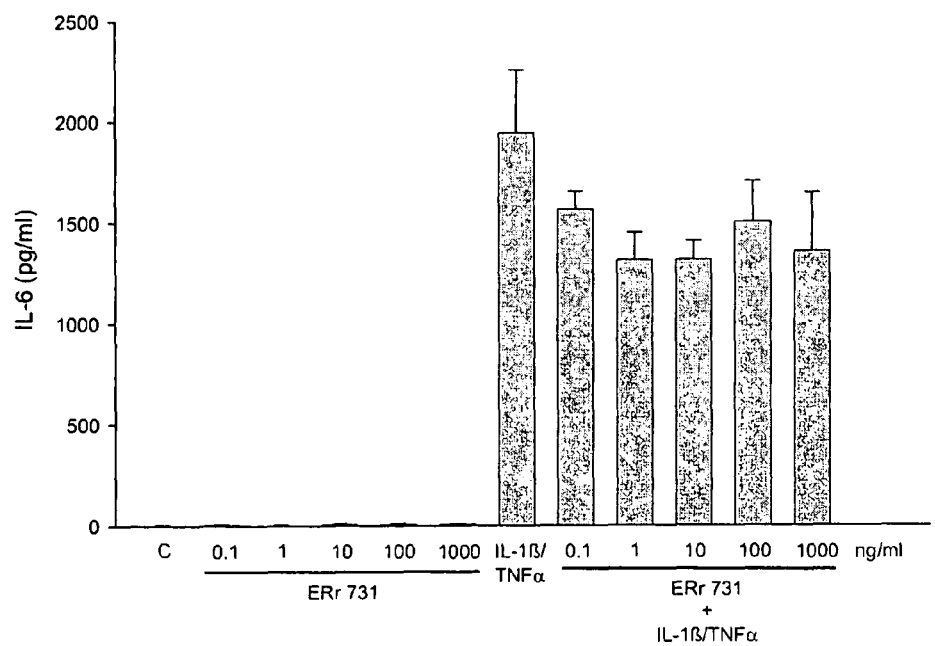
FIG. 5 shows the reduction in IL-6 production, stimulated by administration of the cytokines IL-1β and TNFα, in the human lung carcinoma cell line A549 by the active ingredient combination ERr 731®.

The respective extract concentrations (stock: 10 mg/ml in DMSO; tested concentrations: 0.1 ng/ml to 10 μg/ml) are evident from FIG. 5. During the stimulation, the DMSO concentration resulting from the highest final concentration of ERr 731β in the respective test series was generated in all culture mixtures (0.1% DMSO with 10 μg/ml, 0.01% DMSO with 1 μg/ml).

After incubation for 24 hours, the culture supernatants were removed by centrifugation and the relevant IL-6 concentrations in the cell-free supernatants (three dishes for each condition) were measured by duplicate determination using a specific ELISA for human IL-6.

The IL-1β/TNFα combination led in all test series to a robust induction of IL-6. The stimulatability of the A549 cells by IL-1β/TNFα varied on individual test days between 1000 pg/ml and 5000 pg/ml. The effects of ERr 731® showed no correlation to the strength of the initial stimulation in the test series.

A representative test result is depicted in appended FIG. 5:

It is seen that the inhibition of IL-6 release is about 28% with all ERr 731® concentrations. It was thus surprisingly possible for the first time to show that ERr 731®, i.e. its ingredients rhaponticin and rhapontigenin, bring about a partial reduction in IL-6 release from A549 cells.

The observed effect on IL-6 production is surprising because it has previously been assumed that glycosidic hydroxystilbenes like those present in the active ingredient combination of the invention too have no effect on the mediator production in these cells (Donelly et al. Anti-inflammatory effects of resveratrol in lung epithelial cells: molecular mechanisms. Am J Physiol Lung Cell Mol Physiol 2004; 287: L774-L783).

This is particularly important for the therapy of estrogen-independent tumors (breast, prostate carcinoma).

Test Example 4

Estrogenic Activity of ERr 731® in ERα-Expressing Cell Systems

It was intended to answer the question of whether ERr 731® also activates ERα in addition to Erβ or is specific for ERβ. The extract ERr 731® was therefore investigated, comparing with estradiol, for the estrogenic activity in established model systems.

Test A:

In a first series of experiments, a recombinant yeast screen was used (cf. E. Routledge and J. P. Sumpter, Östrogenic activity of surfactants and some of their degradation products assessed using a recombinant yeast screen, Envirom. Tox. Chem. 1996).

Saccharomyces cerevisiae cells were stably transfected with human ERα both with a reporter gene consisting of the respective responsive promoter element fused to the LacZ gene which codes for β-galactosidase. Estrogen treatment (with estrogen or with a substrate having an estrogen-like effect) of the cells activates, mediated by the estrogen receptor, β-galactosidase, leading to a red coloration of the yeast cells, which can be measured at 565 nm. The test results are summarized in FIG. 6a.

Test B:

In a second series of experiments, the data of the estrogenicity measurement were verified by determining the induction of alkaline phosphatase in Ishikawa cells (human endometrial adenocarcinoma cells) which had been transfected with an ERα-containing reporter gene construct. The activity of alkaline phosphatase, which is assessed using the chromogenic substrate 4-nitrophenyl phosphate, represents an ERα-mediated response.

The test is based on the description by Holinka C F, Hata H, Kuramoto H, Gurpide E (1986) Effects of steroid hormones and antisteroids on alkaline phosphatase activity in human endometrial cancer cells (Ishikawa Line). Cancer Res. 46: 2771-2774, and modifications described in Wober J, Weiβ-wange I, Vollmer G (2002) Stimulation of alkaline phosphatase activity in Ishikawa cells induced by various phytoestrogens and synthetic estrogens. J. Steroid Biochem. Mol. Biol. 83:227-233.

Table 2 presents the concentrations for the positive control (estradiol) and the test substances used in the assay.

TABLE 2

| Test substance | Concentration (M)[1] |
|---|---|
| Estradiol | $10^{-6}$ |
| Resveratrol | $10^{-8}$-$10^{-5}$ |
| trans-Rhapontigenin | $10^{-8}$-$10^{-5}$ |
| Deoxyrhapontigenin | $10^{-8}$-$10^{-5}$ |
| Piceatannol | $10^{-7}$-$10^{-5}$ |
| cis-Rhapontigenin | $10^{-8}$-$10^{-5}$ |
| Extract ERr 731 ® | 0.00001-10 |

[1]Exception: The concentration for the extract ERr 731 ® is indicated in µg/ml

Figure 6A:
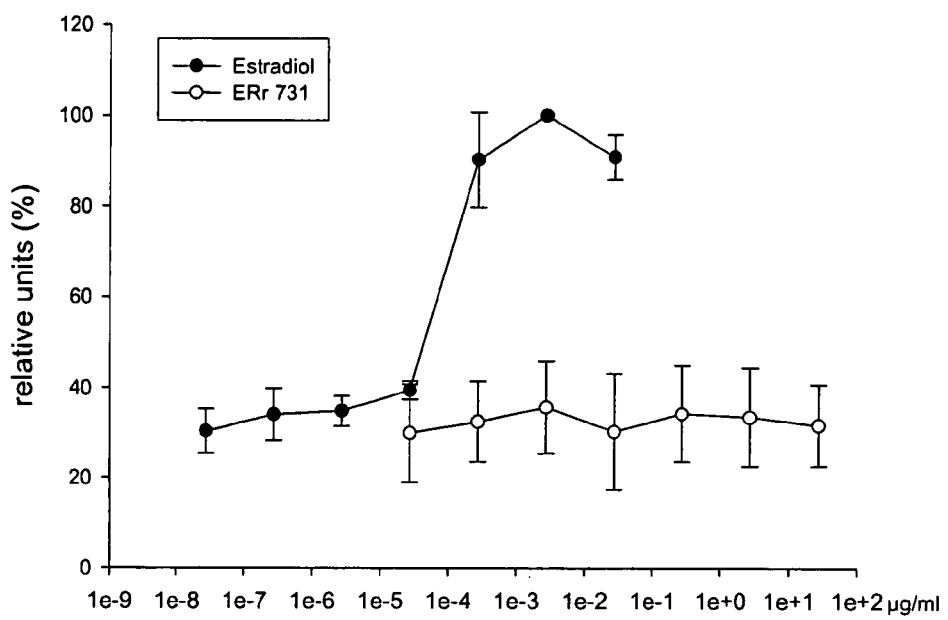
FIG. 6 shows the experimental result on ERα activation with ERr 731®. The active ingredient combination does not activate ERα either in the Ishikawa human endometrial carcinoma line (FIG. 6b) (*=p<0.001) or in yeast cells (FIG. 6a**), both of which were transfected with ERα.
Figure 6B:
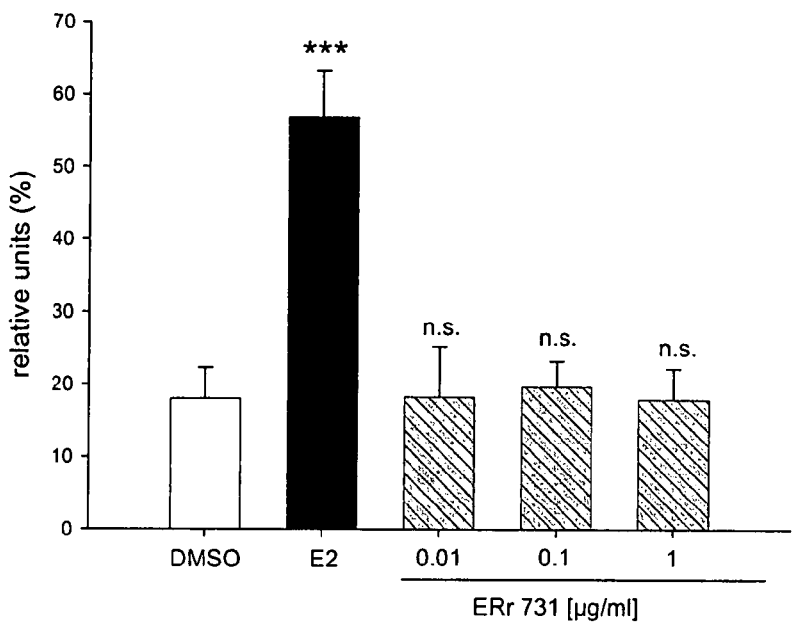

The results of test B are depicted in FIG. 6b for ERr 731®.

Both tests are conclusive because all the positive and negative controls show their predicted effects (cf. FIGS. 6a and b). The results of the two test systems described above demonstrate that neither ERr 731® nor its ingredients and metabolites have a significant effect on the activation of ERα in the cell systems used here. It can thus be assumed that the activity of ERr 731®, especially in endometrial cells, is based on a molecular mechanism independent of ERα.

In summary, it can be stated that the active ingredient composition of the invention has no unwanted ERα-activating effect in endometrial cells but, on the contrary, specifically activates the ERβ(cf. test example 2, above).

Test Example 5

Antiandrogenic Activity of the Ingredients and Metabolites of ERr 731® in an Androgen Receptor-Expressing Yeast Cell System A recombinant yeast screen (E. Routledge and J. P. Sumpter, Östrogenic activity of surfactants and some of their degradation products assessed using a recombinant yeast screen, Envirom. Tox. Chem. 1996.) was used in a series of experiments. The Saccharomyces cerevisiae cells were stably transfected with human androgen receptor and with a reporter gene consisting of the respective response element fused to the LacZ gene which codes for β-galactosidase.

Firstly, a thawed yeast stock culture was grown in 52 ml of growth medium at 28-32° C. as overnight culture with shaking for 24 h. The next morning, 0.5 ml of the overnight culture with an optical density (OD) of 1 was taken for the test culture and put with new 52 ml of growth medium+CPRG enzyme substrate. 1-2 µl portions of the substance dissolved in ethanol or DMSO (quadruplicate) were pipetted into the wells of the 96 microtiter plates. Dihydrotestosterone (DHT) served as standard substance. The mixture of yeasts and test medium was then shaken cautiously and 200 µl of the test culture was pipetted into each well and incubated at 32° C. for 2-3 days. After the incubation for 2-3 days, the color was measured at 565 nm and the turbidity at 690 mm.

The androgenic or antiandrogenic activity was measured via determination of β-galactosidase, which leads to a red coloration of the yeast cells, which can be measured at 565 nm. Table 3 indicates the concentrations of the positive control (DHT) and of the test substances used in the assay.

TABLE 3

| Test substance | Concentration (M) |
|---|---|
| DHT | $10^{-12}$-$10^{-6}$ |
| Deoxyrhapontigenin | $10^{-11}$-$10^{-5}$ |
| Piceatannol | $10^{-10}$-$10^{-5}$ |

Figure 7A:
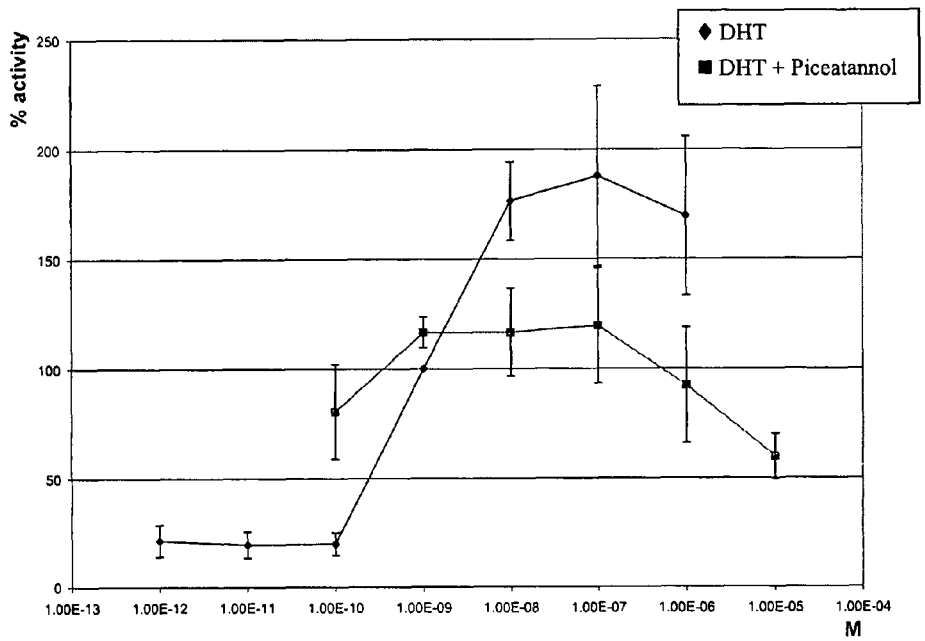
FIG. 7A; dihydrotestosterone (DHT) in the presence of piceatannol.
Figure 7B:
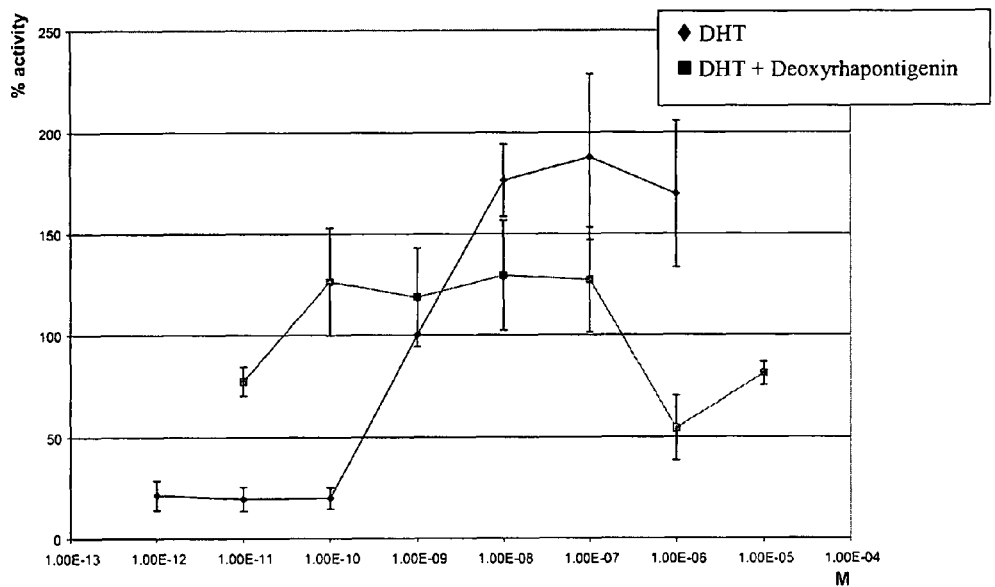
FIG. 7B: DHT in the presence of deoxyrhapontigenin

It was established according to the invention in these experiments that not only certain metabolites (piceatannol) but also ingredients (deoxyrhapontigenin) of ERr 731® exhibit antiandrogenic effects in this cell culture system by preventing the binding of DHT to the androgen receptor in a concentration range of 1-10 µM (FIG. 7 A, B).

Figure 7C:
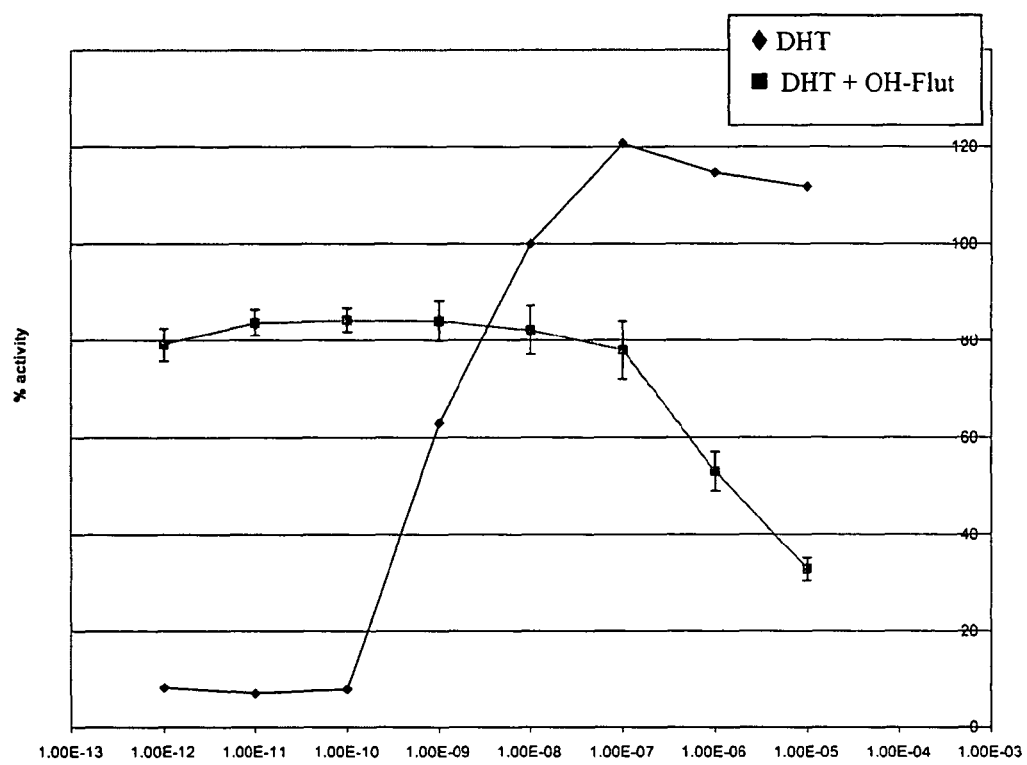
FIG. 7C: DHT in the presence of hydroxyflutamide (positive control).

The validity of this test was demonstrated using the competitive androgen receptor antagonist hydroxyflutamide as positive control (FIG. 7C).

The test results indicate that in particular also ingredients of ERr 731® interact with various androgen receptor-mediated signalling pathways which may lead to prostate cancer and LUTS.

In a second series of experiments in this cell culture system (tests not shown), it was found that neither individual ingredients nor the abovementioned metabolites of ERr 731® nor the complete extract ERr 731® itself activate the androgen receptor. This means that ERr 731® and its ingredients or metabolites have no androgenic effect.

The invention claimed is:

1. A method of treating depression or anxiety in subjects, wherein the subjects are female non-menopausal patients or male patients, the method comprising administering to the subject an effective amount of a hydroxystilbene-containing active ingredient combination comprising rhaponticin and deoxyrhaponticin in a ratio of about 10:1 to 1:10 by weight or ester and ether derivatives thereof and stereoisomeric forms thereof, in each case in the form of their salts or in the phenol form, wherein said hydroxystilbene-containing active ingredient combination contains 91 to 100% by weight of a total content of rhaponticin and deoxyrhaponticin.

2. The method of claim 1, wherein the active ingredient combination comprises a) a total hydroxystilbene content of 94 to 97% by weight; and/or b) an aglycone content of less than 5% by weight; and/or c) a content of less than 0.5% by weight of anthraquinone and/or anthraquinoids.

3. The method of claim 1, wherein the hydroxystilbene components of the active ingredient combination are chemically synthesized or isolated from plants.

4. The method of claim 1, wherein the active ingredient combination further comprises rhapontigenin, and/or deoxyrhapontigenin.

5. The method of claim 1, wherein the active ingredient combination is substantially free of aglycone derivatives of rhaponticin and deoxyrhaponticin.

6. The method of claim 1, wherein the active ingredient combination further comprises 0-2% by weight trans-rhapontigenin and 0-2% by weight deoxyrhapontigenin.

7. The method of claim 1, wherein the active ingredient or the active ingredient combination is obtained from plants of the genus *Rheum* spp, *Astragalus* spp, *Cassia* spp or *Picea* spp.

8. The method of claim 1, wherein the active ingredient or the active ingredient combination is obtained from roots and/or other plant parts of *Rheum rhaponticum*.

9. The method of claim 1, wherein the active ingredient combination is contained in a composition selected from the group consisting of dietary supplements and dietetic food products.

10. The method of claim 1, wherein the active ingredient combination reduces IL-6 serum level and/or activates ERβ in vitro or in vivo.

* * * * *